US010716606B2

(12) United States Patent
Appenzeller et al.

(10) Patent No.: US 10,716,606 B2
(45) Date of Patent: Jul. 21, 2020

(54) BONE FIXATION SYSTEM

(71) Applicant: Depuy Synthes Products, Inc., Raynham, MA (US)

(72) Inventors: Andreas Appenzeller, Biel (CH); Daniel Fluri, Bettlach (CH)

(73) Assignee: DePuy Synthes Products, Inc., Raynham, MA (US)

( * ) Notice: Subject to any disclaimer, the term of this patent is extended or adjusted under 35 U.S.C. 154(b) by 660 days.

(21) Appl. No.: 14/422,844

(22) PCT Filed: Aug. 23, 2013

(86) PCT No.: PCT/US2013/056348
§ 371 (c)(1),
(2) Date: Feb. 20, 2015

(87) PCT Pub. No.: WO2014/031938
PCT Pub. Date: Feb. 27, 2014

(65) Prior Publication Data
US 2015/0223853 A1 Aug. 13, 2015

Related U.S. Application Data

(63) Continuation of application No. 13/832,518, filed on Mar. 15, 2013, now Pat. No. 10,004,603, and a
(Continued)

(51) Int. Cl.
*A61B 17/80* (2006.01)
*A61B 17/86* (2006.01)

(52) U.S. Cl.
CPC ...... *A61B 17/8052* (2013.01); *A61B 17/8047* (2013.01); *A61B 17/8057* (2013.01);
(Continued)

(58) Field of Classification Search
CPC ............ A61B 17/6475; A61B 17/6466; A61B 2002/448; A61B 2/4455; A61B 17/7049;
(Continued)

(56) References Cited

U.S. PATENT DOCUMENTS 4,429,690 A 2/1984 Angelino-Pievani
4,467,793 A 8/1984 Ender
(Continued)

FOREIGN PATENT DOCUMENTS

CA 2626694 C 8/2011
CN 1337864 2/2002
(Continued)

OTHER PUBLICATIONS

U.S. Appl. No. 13/832,518, filed Mar. 15, 2013, Appenzeller et al.
(Continued)

*Primary Examiner* — Christopher D. Prone
(74) *Attorney, Agent, or Firm* — BakerHostetler

(57) ABSTRACT

A bone fixation system has a bone implant with an implant body. The implant body defines an upper surface, a bone-facing surface spaced from the upper surface along a transverse direction, and at least one aperture defined by an inner wall. A bone fixation element is configured for insertion at least partially through the aperture. The bone fixation element has a head and a shaft that extends relative to the head in a distal direction. The head defines a ridge and at least one thread that is spaced from the ridge in the distal direction. The ridge is configured to compress a bone implant against the at least one thread so as to fixedly retain the bone implant with respect to the head.

19 Claims, 11 Drawing Sheets

Related U.S. Application Data continuation of application No. 13/832,364, filed on Mar. 15, 2013, now Pat. No. 9,452,005.

(60) Provisional application No. 61/786,937, filed on Mar. 15, 2013, provisional application No. 61/787,082, filed on Mar. 15, 2013, provisional application No. 61/692,673, filed on Aug. 23, 2012.

(52) U.S. Cl.
CPC ...... *A61B 17/8061* (2013.01); *A61B 17/8605* (2013.01); *A61B 17/869* (2013.01)

(58) Field of Classification Search
CPC .............. A61B 17/705; A61B 17/7002; A61B 17/7005
See application file for complete search history.

(56) References Cited

U.S. PATENT DOCUMENTS

| | | | |
|---|---|---|---|
| 5,281,225 A | 1/1994 | Vincenzi | |
| 5,324,307 A | 6/1994 | Jarrett et al. | |
| 5,725,532 A | 3/1998 | Shoemaker | |
| 5,766,176 A | 6/1998 | Duncan | |
| 5,913,896 A | 6/1999 | Boyle et al. | |
| 6,203,545 B1 | 3/2001 | Stoffella | |
| 6,306,136 B1 | 10/2001 | Baccelli | |
| 6,436,099 B1* | 8/2002 | Drewry ............... A61B 17/7022 606/300 |
| 6,506,191 B1 | 1/2003 | Joos | |
| 6,558,388 B1 | 5/2003 | Bartsch et al. | |
| 7,776,076 B2 | 8/2010 | Grady et al. | |
| 8,118,846 B2 | 2/2012 | Leither et al. | |
| 8,172,884 B2 | 5/2012 | Bouman | |
| 8,343,152 B2 | 1/2013 | Gonzalez-Hernandez | |
| 2003/0023241 A1 | 1/2003 | Drewry | |
| 2003/0153918 A1 | 8/2003 | Putnam et al. | |
| 2004/0102776 A1 | 5/2004 | Huebner | |
| 2004/0236170 A1 | 11/2004 | Kim | |
| 2005/0049595 A1 | 3/2005 | Suh et al. | |
| 2005/0070904 A1 | 3/2005 | Gerlach et al. | |
| 2005/0101961 A1 | 5/2005 | Huebner et al. | |
| 2005/0136764 A1 | 6/2005 | Sherman et al. | |
| 2005/0261688 A1 | 11/2005 | Grady, Jr. et al. | |
| 2006/0009771 A1 | 1/2006 | Orbay et al. | |
| 2006/0235399 A1 | 2/2006 | Carls et al. | |
| 2006/0189992 A1 | 8/2006 | Medoff | |
| 2006/0235400 A1* | 10/2006 | Schneider ........... A61B 17/8052 606/287 |
| 2006/0264946 A1 | 11/2006 | Young | |
| 2006/0276793 A1 | 12/2006 | Berry | |
| 2007/0173834 A1 | 7/2007 | Thakkar | |
| 2007/0225715 A1 | 9/2007 | Deffenbaugh et al. | |
| 2007/0233122 A1 | 10/2007 | Denis et al. | |
| 2008/0065074 A1 | 3/2008 | Yeung et al. | |
| 2008/0188899 A1 | 8/2008 | Bottlang et al. | |
| 2008/0269745 A1 | 10/2008 | Justin | |
| 2008/0281363 A1 | 11/2008 | Ullman et al. | |
| 2009/0069851 A1 | 3/2009 | Gillard et al. | |
| 2009/0264936 A1 | 10/2009 | Gonzalez-Hernandez et al. | |
| 2010/0036430 A1* | 2/2010 | Hartdegen ......... A61B 17/1728 606/281 |
| 2010/0063549 A1 | 3/2010 | Orbay et al. | |
| 2010/0305569 A1 | 12/2010 | Leuenberger et al. | |
| 2011/0009912 A1 | 1/2011 | Gonzalez-Hernandez et al. | |
| 2011/0230914 A1 | 9/2011 | Engelman et al. | |
| 2011/0257685 A1 | 10/2011 | Hay et al. | |
| 2011/0270312 A1 | 11/2011 | Assell et al. | |
| 2011/0282393 A1 | 11/2011 | Gerlach et al. | |
| 2012/0004690 A1 | 1/2012 | Gonzalez-Hernandez | |
| 2012/0109128 A1 | 5/2012 | Frigg | |
| 2012/0136396 A1 | 5/2012 | Baker et al. | |
| 2012/0239036 A1 | 9/2012 | Voisard | |
| 2012/0330365 A1 | 12/2012 | Lin et al. | |
| 2014/0039561 A1 | 2/2014 | Weiner | |
| 2014/0058391 A1 | 2/2014 | Fluri Daniel | |
| 2014/0058455 A1 | 2/2014 | Appenzeller et al. | |
| 2014/0058510 A1 | 2/2014 | Appenzeller et al. | |
| 2015/0018889 A1 | 1/2015 | Schneider | |

FOREIGN PATENT DOCUMENTS

| | | |
|---|---|---|
| CN | 1482890 A | 3/2004 |
| CN | 1631325 | 6/2005 |
| CN | 1694653 | 11/2005 |
| CN | 1764418 A | 4/2006 |
| CN | 1911454 A | 2/2007 |
| CN | 1988854 | 6/2007 |
| CN | 2922820 | 7/2007 |
| CN | 101040794 A | 9/2007 |
| CN | 101123922 A | 2/2008 |
| CN | 101394802 A | 3/2009 |
| CN | 101801293 A | 8/2010 |
| CN | 102008347 A | 4/2011 |
| CN | 102421383 A | 4/2012 |
| CN | 102458284 | 5/2012 |
| CN | 102470197 A | 5/2012 |
| DE | 202005019277 | 2/2006 |
| EP | 0401650 | 12/1990 |
| EP | 0743045 | 11/1996 |
| EP | 0873718 | 10/1998 |
| EP | 0882431 | 12/1998 |
| EP | 1764052 A1 | 3/2007 |
| EP | 2887894 A1 | 7/2015 |
| FR | 2722545 | 1/1996 |
| FR | 2728155 | 6/1996 |
| JP | 57-081333 A | 5/1982 |
| JP | 2002-541968 A | 12/2002 |
| JP | 2006-506197 A | 2/2006 |
| JP | 2007-507296 A | 3/2007 |
| JP | 2007-083046 A | 4/2007 |
| JP | 2007-514507 A | 6/2007 |
| JP | 2008-535561 A | 9/2008 |
| JP | 2010-517673 A | 5/2010 |
| JP | 2011-500166 A | 1/2011 |
| JP | 2011-529748 A | 12/2011 |
| JP | 2015-526204 A | 9/2015 |
| RU | 2133593 C1 | 7/1999 |
| RU | 2171651 C1 | 8/2001 |
| RU | 2245685 C2 | 2/2005 |
| RU | 2253395 C1 | 6/2005 |
| RU | 108948 U1 | 10/2011 |
| SU | 1367961 A1 | 1/1988 |
| TW | 201219004 A | 5/2012 |
| TW | 201221258 A | 6/2012 |
| WO | WO 87/02572 | 5/1987 |
| WO | WO 98/33448 | 8/1998 |
| WO | 2008/097403 A1 | 8/2008 |
| WO | WO 2012/103164 | 8/2012 |
| WO | 20141031935 A1 | 2/2014 |

OTHER PUBLICATIONS

U.S. Appl. No. 13/974,310, filed Aug. 23, 2013, Appenzeller et al.
International Patent Application No. PCT/US2013/056345: International Search Report dated Oct. 23, 2013, 10 pages.
International Patent Application No. PCT/US2013/056367: International Search Report dated Oct. 23, 2013, 10 pages.
International Patent Application No. PCT/US2013/056348: Invitation to Pay Additional Fees dated Oct. 23, 2013, 6 pages.
International Patent Application No. PCT/US2013/056374: International Search Report dated Nov. 5, 2013, 10 pages.
International Patent Application No. PCT/US2013/056348: International Search Report dated Jan. 17, 2014, 16 pages.

* cited by examiner

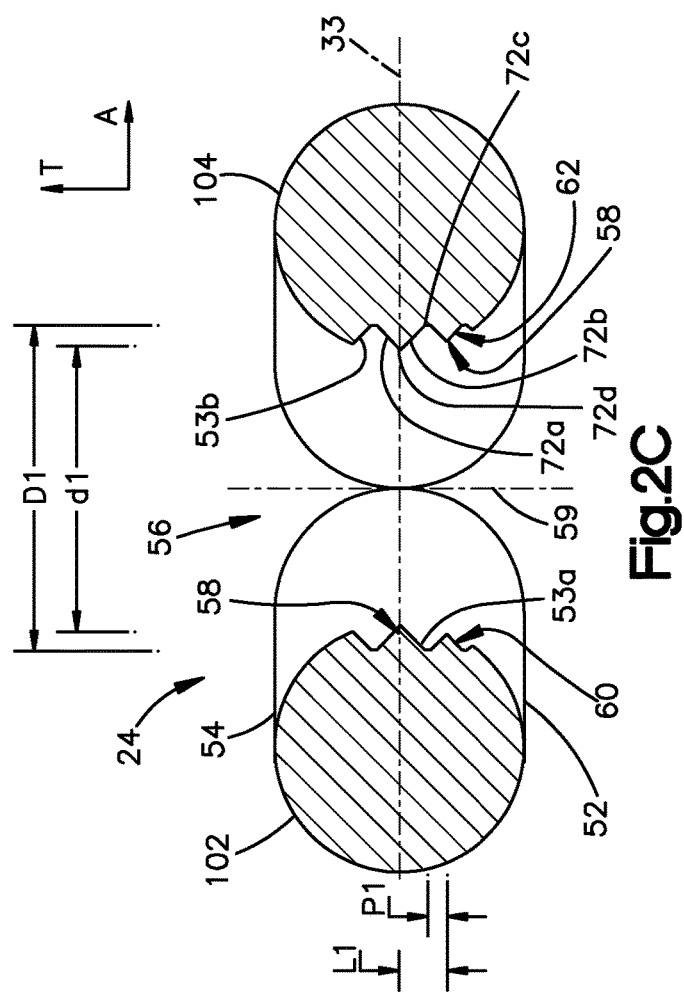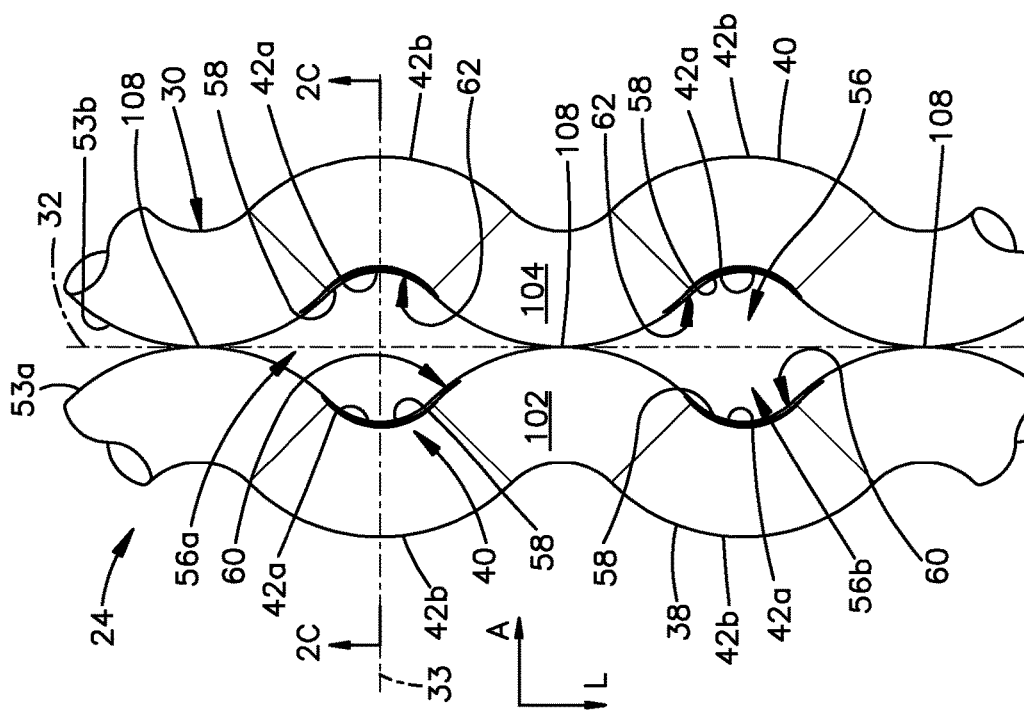

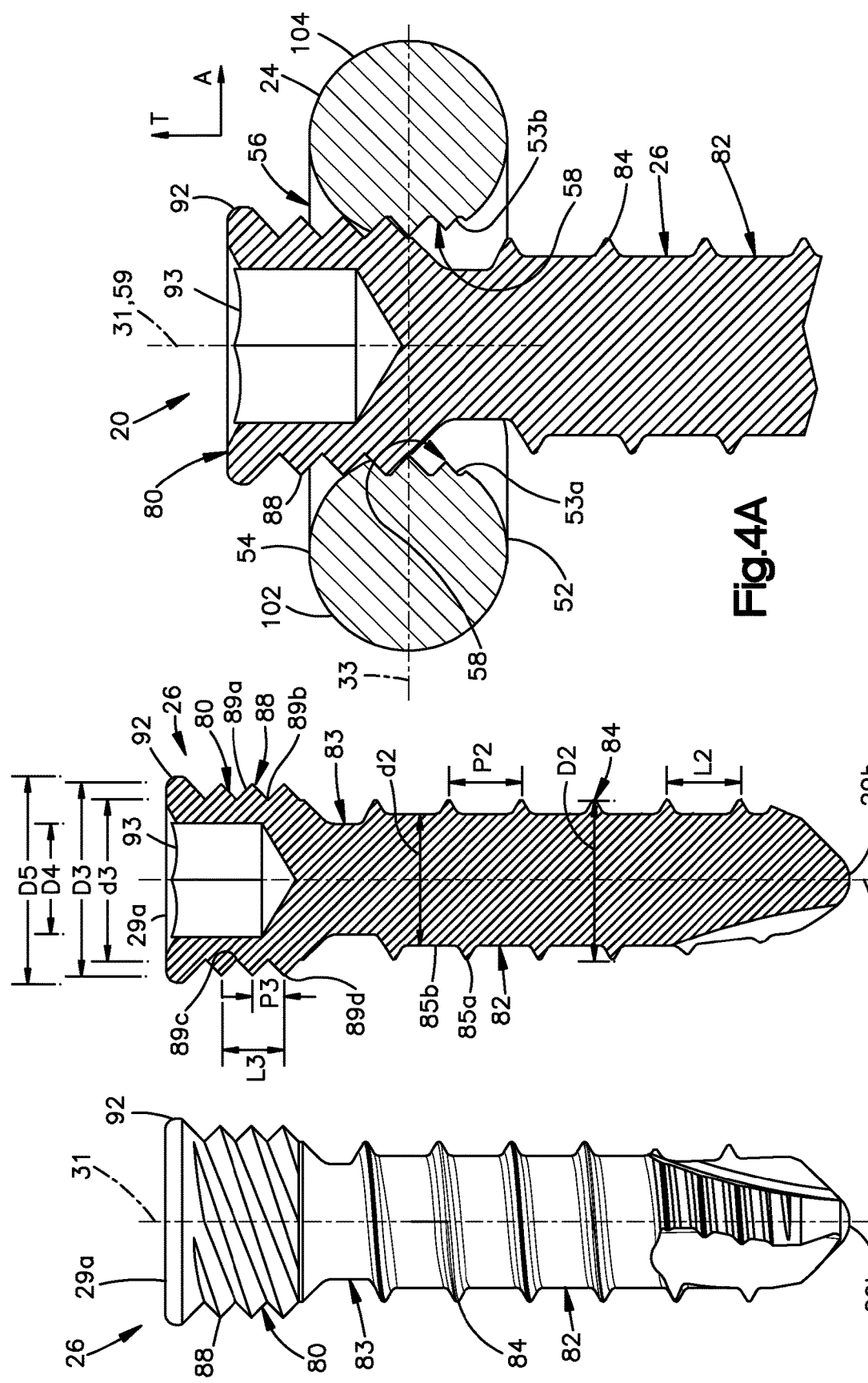

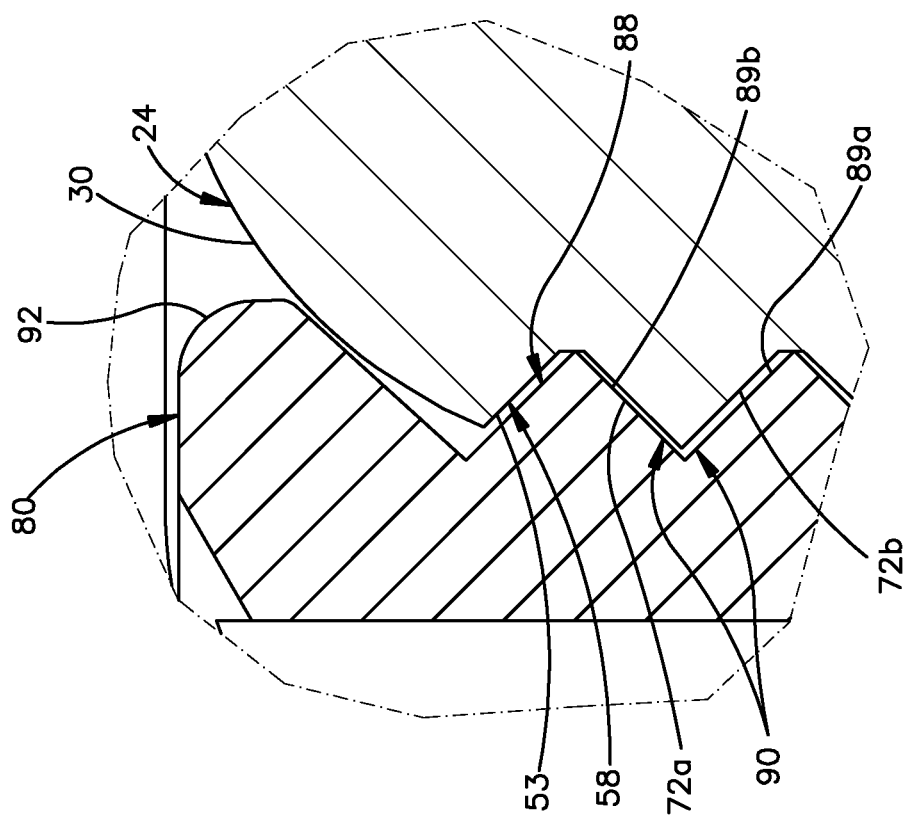
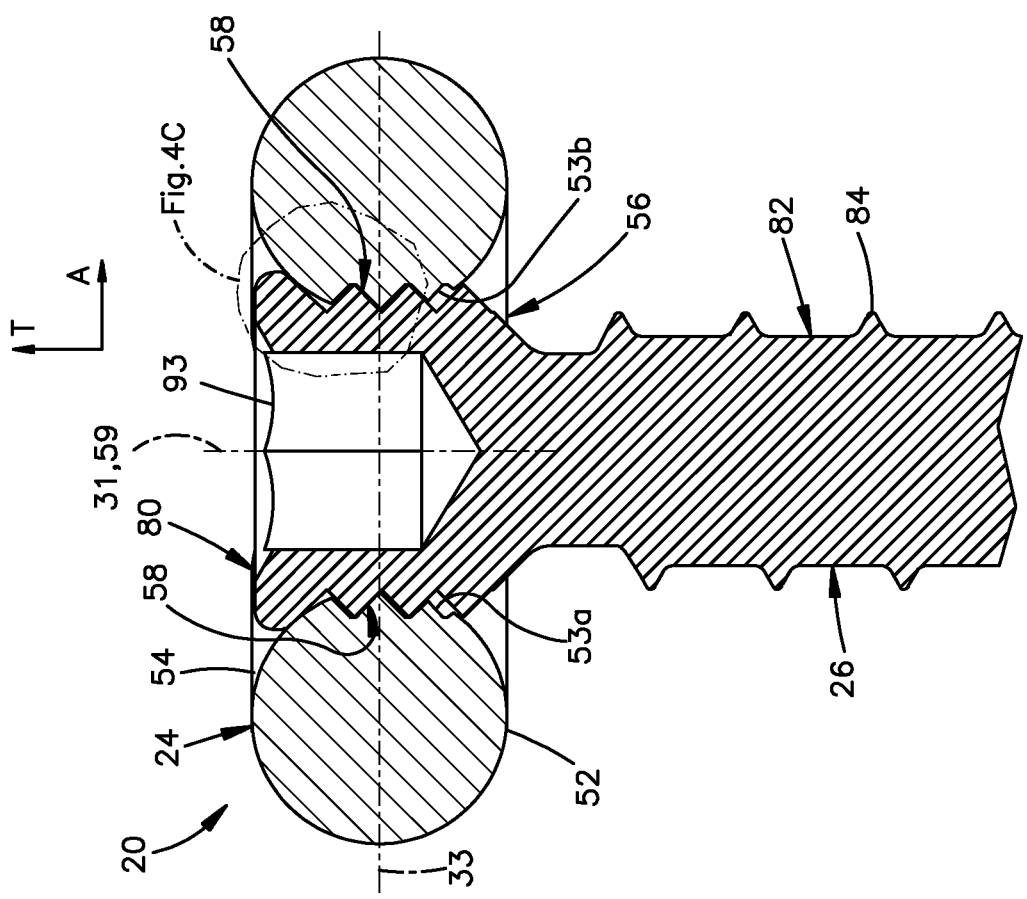
Fig.4C
Fig.4B

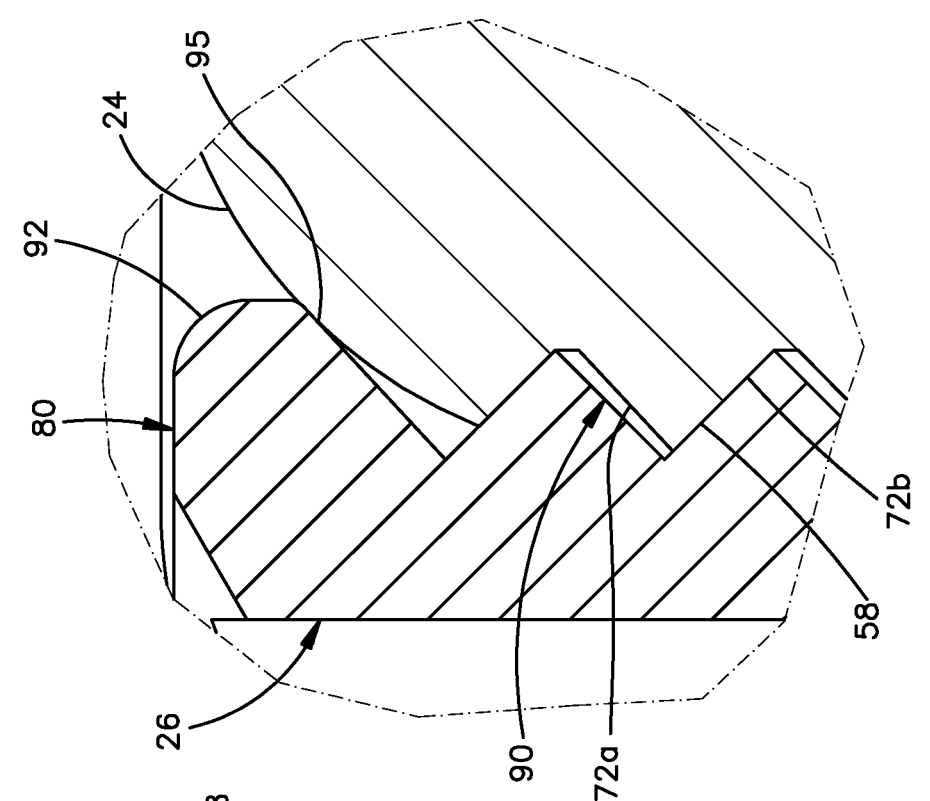
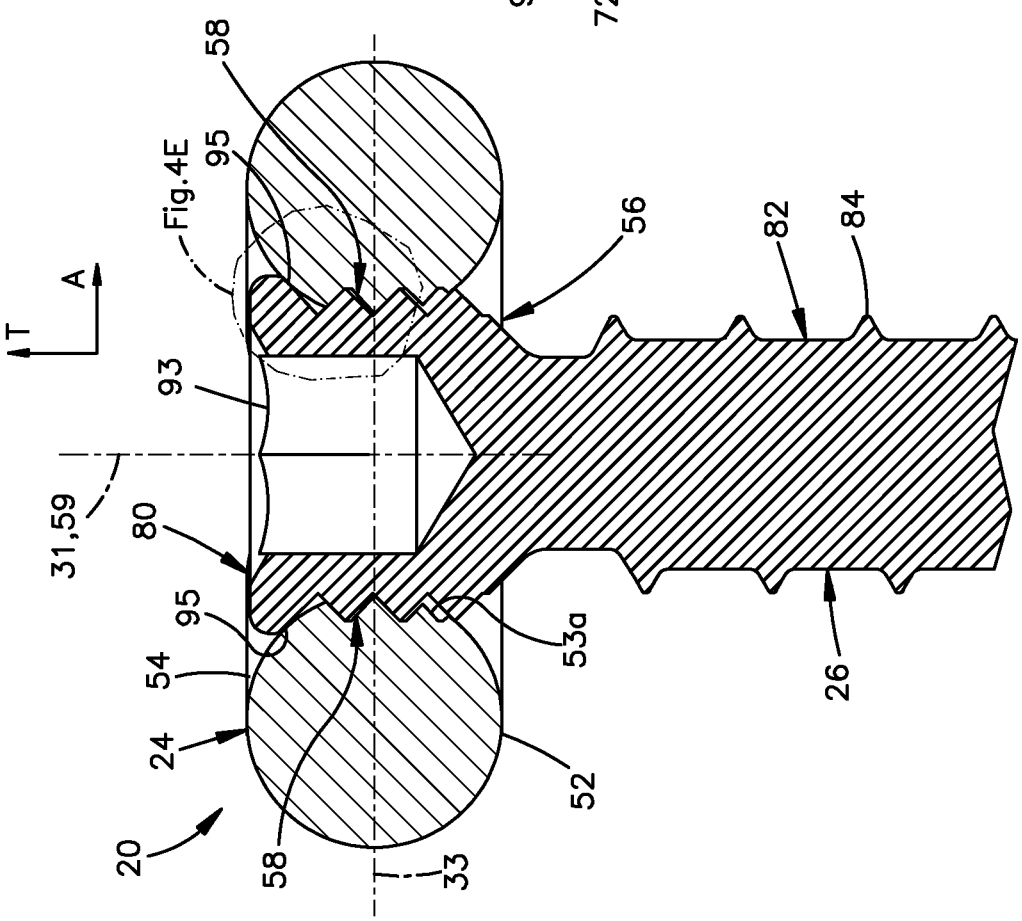
Fig.4E
Fig.4D

BONE FIXATION SYSTEM

CROSS-REFERENCE TO RELATED APPLICATIONS

This application is a National Stage Application filed under 35 U.S.C. 371 of International Application No. PCT/US2013/056348, filed Aug. 23, 2013, which claims priority to U.S. patent application Ser. No. 13/832,518 filed Mar. 15, 2013, U.S. Patent Application Ser. No. 61/786,937 filed Mar. 15, 2013, U.S. patent application Ser. No. 13/832,364 filed Mar. 15, 2013, U.S. Patent Application Ser. No. 61/787,082 filed Mar. 15, 2013 and U.S. Patent Application Ser. No. 61/692,673 filed Aug. 23, 2012, the disclosure of each of which is hereby incorporated by reference as if set forth in its entirety herein.

TECHNICAL FIELD

The present disclosure relates to a bone fixation system, and particularly to a bone implant and a bone fixation element, methods for coupling a bone implant to a bone fixation element, and methods for bone fixation.

BACKGROUND

Bone implants are designed to help heal bone fractures and/or replace damaged tissue. Principles that guide bone implant design include anatomic reduction of fracture fragments, stable fixation to improve tissue healing, minimal procedural invasiveness to preserve local blood supply, and early and pain-free mobilization so that the patient can return to normal function as soon as possible. These principles have guided the development of many examples of bone implants, such as bone plates, intramedullary nails, vertebral implants, etc., as well as screws and or anchors configured to hold the bone implant in the desired position at the intended tissue site.

SUMMARY

According to one embodiment of the present disclosure, a bone fixation system includes a bone implant and at least one bone fixation element. The bone implant includes an implant body that defines an upper surface and a bone-facing surface opposite the upper surface, and at least one bone fixation aperture that extends through the implant body from the upper surface to the bone-facing surface. The bone fixation aperture is at least partially defined by a threaded inner wall. The bone fixation element includes a head and a shaft that extends with respect to the head in a distal direction and is configured to be driven into a fixation site. The bone fixation element further defines a stop surface and the head defines a threaded region that is spaced from the stop surface along the distal direction. The threaded region is configured to threadedly engage the threaded inner wall as the bone fixation element rotates to advance the head in the distal direction in the aperture until at least a portion of the threaded inner wall is captured between the stop surface and the threaded region.

BRIEF DESCRIPTION OF THE DRAWINGS

The foregoing summary, as well as the following detailed description of illustrative embodiments of the bone fixation system of the present disclosure, is better understood when read in conjunction with the appended drawings. It should be understood, however, that the present disclosure is not limited to the precise schematics and arrangements shown. In the drawings:

FIG. 2B is a top plan view of the bone implant illustrated in FIG. 2A;

FIG. 2C is a cross-sectional elevation view of the bone implant illustrated in FIG. 2B taken along line 2C-2C;

FIG. 3A is a side elevation view of the bone fixation element illustrated in FIG. 1A;

FIG. 3B is a cross-sectional elevation view of the bone fixation element illustrated in FIG. 3A;

FIG. 4A is a cross-sectional elevation view of the bone fixation system illustrated in FIG. 1A, showing insertion of the bone fixation element into a bone fixation aperture of the bone implant;

FIG. 4B is a cross-sectional elevation view of the bone fixation system illustrated in FIG. 4A, but showing the bone fixation element further inserted into the bone fixation aperture so that a stop surface abuts the bone implant;

FIG. 4C is an enlarged cross-sectional elevation view of the bone fixation system illustrated in FIG. 4B, taken at line 4C;

FIG. 4D is a cross-sectional elevation view of the bone fixation system illustrated in FIG. 4B, but showing the bone fixation element further inserted into the bone fixation aperture so that a stop surface is compressed against the bone implant, thereby securing the bone implant with respect to the bone fixation element;

FIG. 4E is an enlarged cross-sectional elevation view of the bone fixation system illustrated in FIG. 4D, taken at line 4E;

DETAILED DESCRIPTION OF ILLUSTRATIVE EMBODIMENTS

Figure 1A:
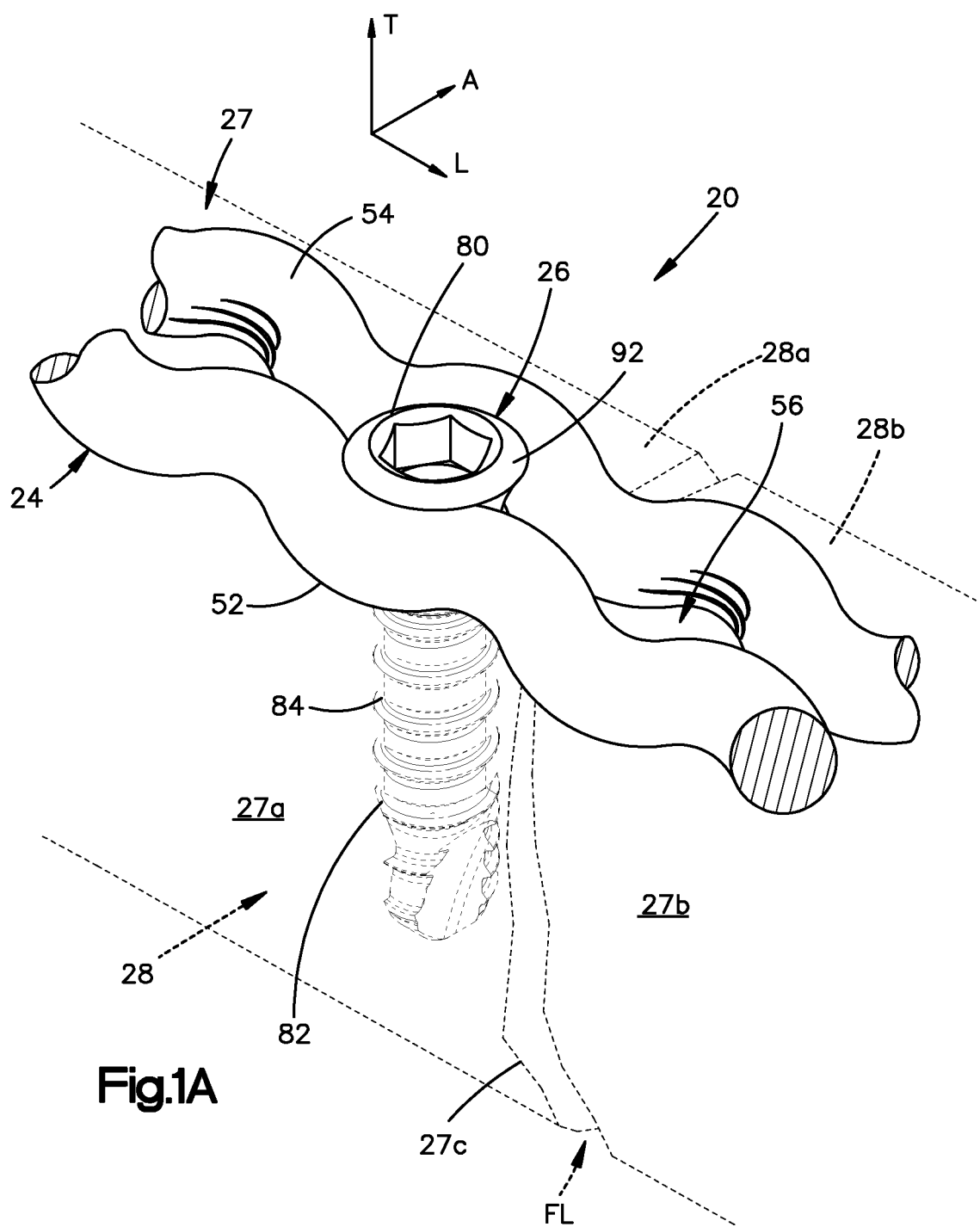
FIG. 1A is a perspective view of a bone fixation system constructed in accordance with one embodiment, including a bone implant and at least one bone fixation element attach to the bone implant and an underlying bone so as to secure the bone implant to the underlying bone.
Figure 1B:
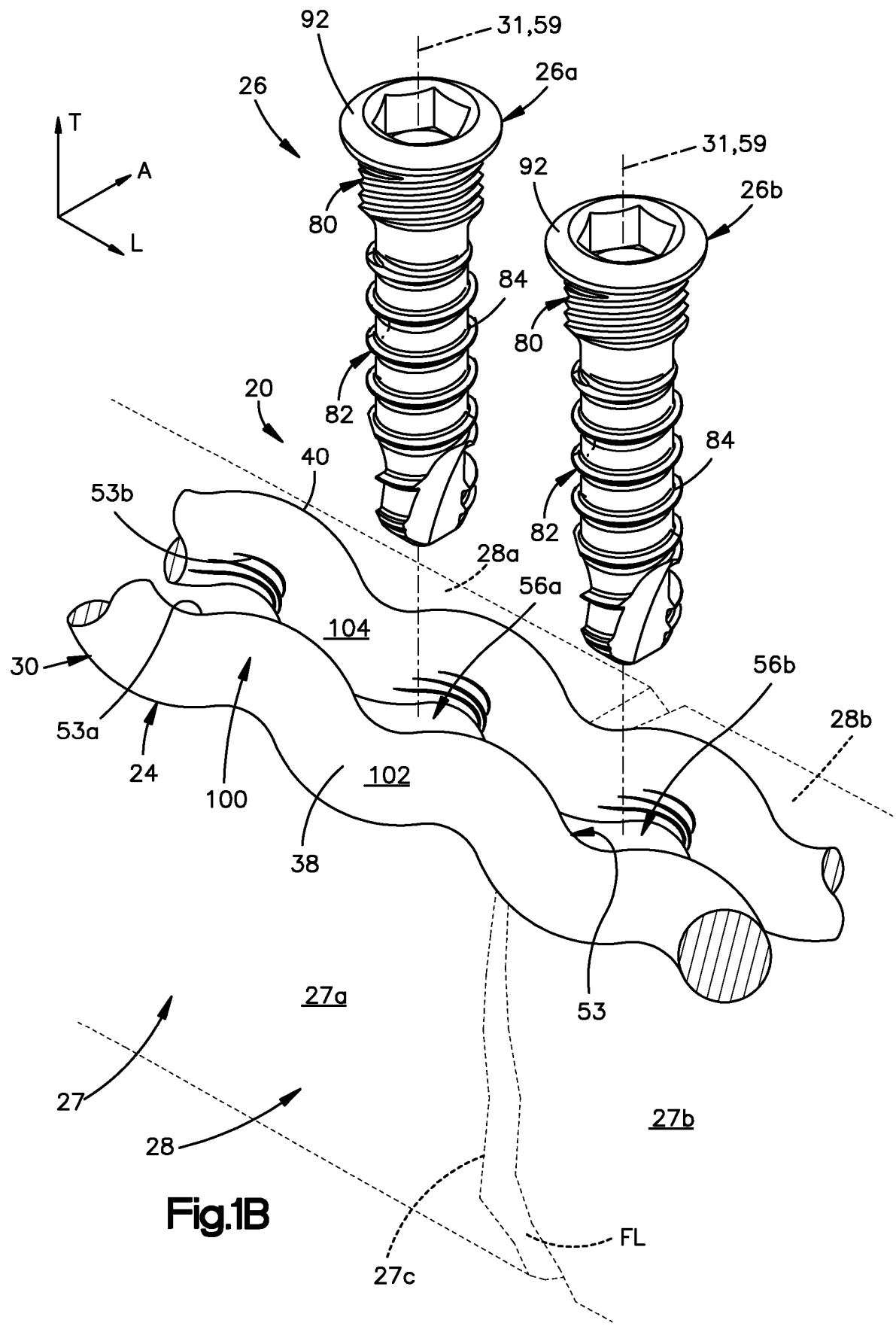
FIG. 1B is an exploded perspective view of the bone fixation system illustrated in FIG. 1A.
Figure 1C:
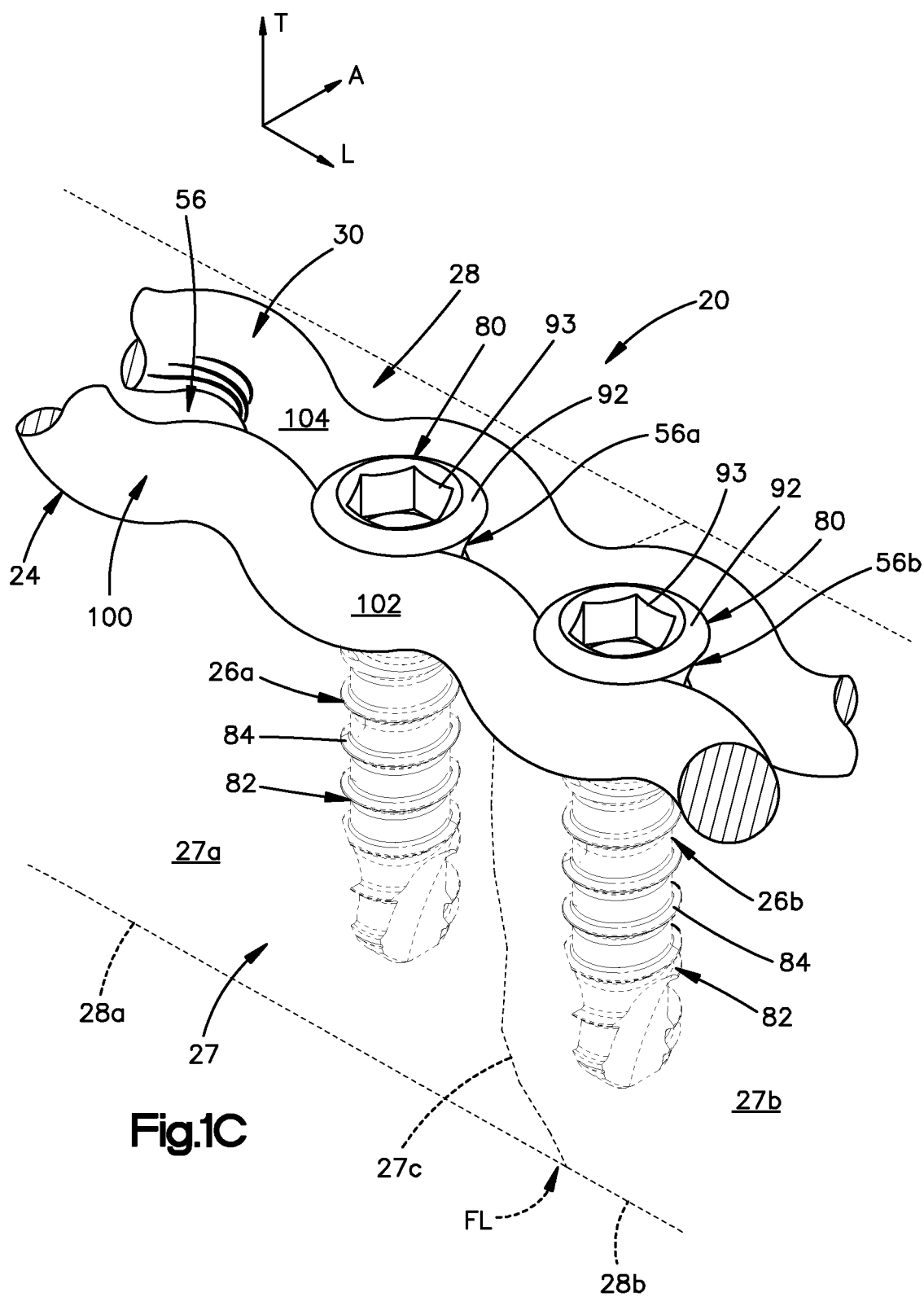
FIG. 1C is a perspective view of a bone fixation system illustrated in FIG. 1A, illustrating a first bone fixation element and a second bone fixation element securing a bone implant to a bone.

Referring to FIGS. 1A-1C, a bone fixation system 20 in accordance with one embodiment is configured to stabilize a bone that has been fractured at one or more fracture locations into a plurality of bone fragments. The bone fixation system 20 includes a bone implant 24 and a bone fixation element 26 configured for insertion at least partially through the bone implant 24 to secure the bone implant 24 to an underlying fixation site 28. The fixation site 28 can be a bone fixation site defined by a bone 27 as illustrated, an implant, or a device configured to receive a bone fixation element. For instance, the bone 27 can define a pair of fixation sites, such as a first fixation site 28*a* of a first bone fragment 27*a* of the bone 27, and a second fixation site 28*b* of a second bone fragment 27*b* of the bone 27. The bone 27 can define a bone gap 27*c*, which can be defined by a fracture location FL, that separates the first bone fragment 27*a* from the second bone fragment 27*b*. The fixation sites 28*a-b* can be located at any anatomical location on a skeletal system. For instance, the fixation sites 28*a-b* can be located on the skull, the vertebral column, any long bone, such as the humerus, femur, tibia, fibula, or any other location on the skeleton system where fixation is desired. The fixation site 28 can also be an additional implant, device or prosthesis configured to receive the bone fixation element therethrough for securement to the bone.

The bone fixation element 26 is configured to be coupled to the bone implant 24 when the bone fixation element 26 is fully inserted in the bone implant 24 as illustrated FIG. 1A. For instance, the bone implant 24 includes an implant body 30 that is elongate substantially along a central implant axis 32 (see FIGS. 2A-2B). The bone implant 24 can be elongate along the central implant axis 32, which can be linear or nonlinear as desired. The implant body 30 includes lateral sides 38 and 40 that are spaced from each other along a lateral implant axis 33 or second direction that can be angularly offset, for instance perpendicular, with respect to the central implant axis 32.

In accordance with one embodiment, the central implant axis 32 can extend along a longitudinal direction L, and the lateral sides 38 and 40 are spaced from each other along the lateral direction A that is substantially perpendicular to the longitudinal direction L. Thus, reference to the longitudinal direction L herein can equally refer to the central implant axis 32, unless otherwise indicated. Further, reference to the lateral direction A herein can equally refer to the lateral implant axis 33 or the second direction, unless otherwise indicated. The implant body 30 can further define a bone facing surface 52 that is configured to face toward the fixation site 28 when the bone implant 24 is secured to the fixation site 28, and an opposed or upper surface 54 that faces away from the fixation site 28 when the bone implant 24 is secured to the fixation site 28. The bone facing surface 52 and the opposed upper surface 54 can be spaced from each other along a transverse direction T that is substantially perpendicular with respect to both the longitudinal direction L and the lateral direction A. The bone facing surface 52 is spaced from the upper surface 54 in a distal direction, and the upper surface 54 is spaced from the bone facing surface in a proximal direction.

The bone implant 24 defines a plurality of bone fixation apertures 56 that extend through the implant body 30 along the transverse direction T from the upper surface 54 to the bone facing surface 52, and at least one inner wall 53 that extends between the upper surface 54 and bone-facing surface 52 and defines each bone fixation aperture 56. At least a portion of each inner wall 53 can be curved as it extends along the transverse direction T. As will be described in more detail below, at least a portion of the inner walls 53 can be threaded so as to threadedly mate with complementary threads of the bone fixation element 26 when the bone fixation element 26 is driven into the respective bone fixation aperture 56.

The bone implant 24 are described herein as extending horizontally along a longitudinal direction "L" and a lateral direction "A", and vertically along a transverse direction "T". Unless otherwise specified herein, the terms "longitu- dinal," "transverse," and "lateral" are used to describe the orthogonal directional components of various bone fixation system components and component axes. It should be appreciated that while the longitudinal and lateral directions are illustrated as extending along a horizontal plane, and that the transverse direction is illustrated as extending along a vertical plane, the planes that encompass the various directions may differ during use. Further, the description refers to bone fixation system components and/or portions of such components that include a "proximal end" and a "distal end." Thus, a "proximal direction" or "proximally" refers to a direction that is oriented generally from the distal end toward the proximal end. A "distal direction" or "distally" refers to a direction that is oriented generally from the proximal end toward the distal end.

Figure 2A:
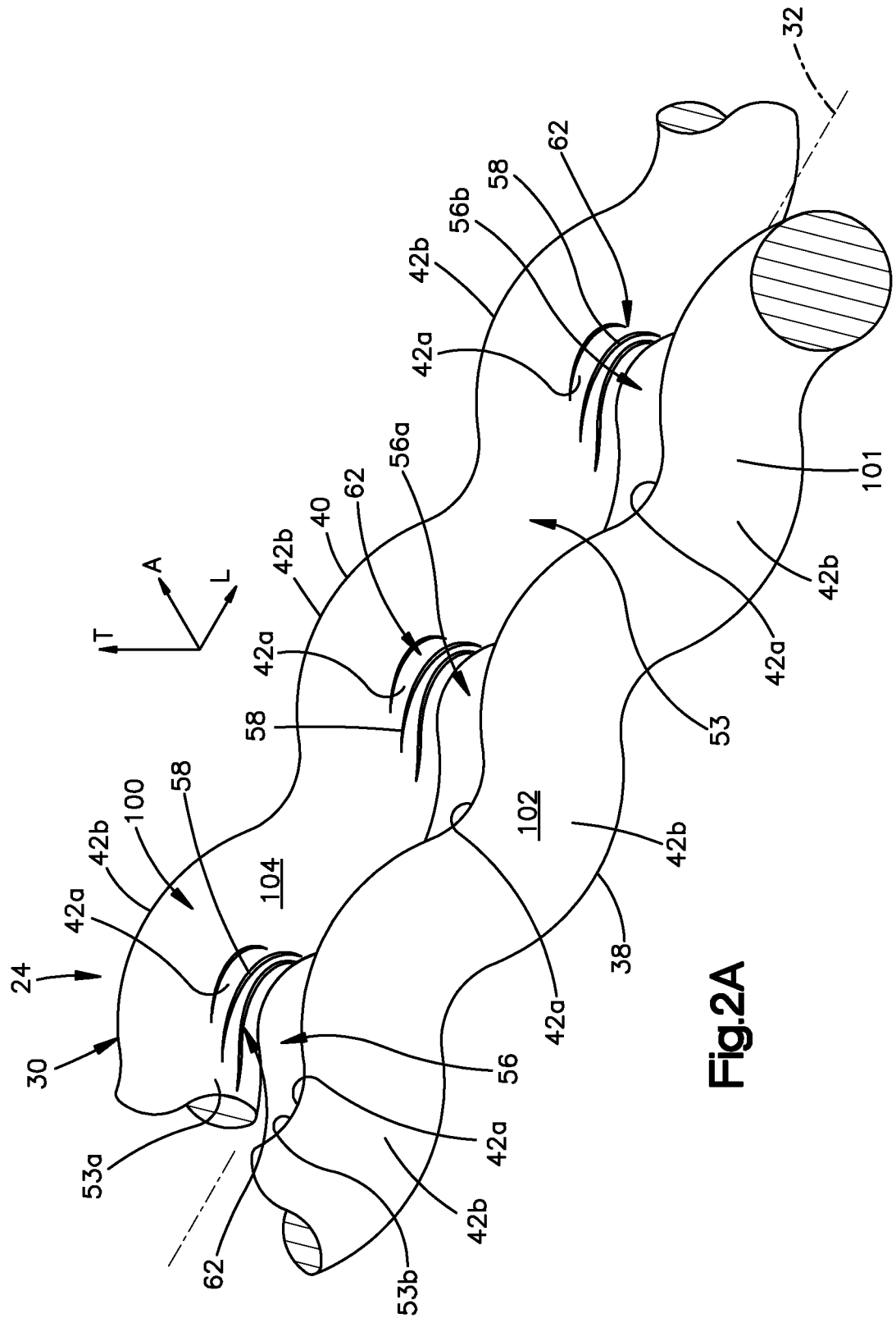
FIG. 2A is a perspective view of the bone implant illustrated in FIG. 1A.

Referring now to FIGS. 2A-2C, the bone implant 24 includes at least one wire 100 that is shaped to define the implant body 30 including the plurality of apertures 56 that extend though implant body 30 from the upper surface 54 to the bone-facing surface 52 along a central aperture axis 59 that can be oriented in the transverse direction T. The bone implant 24 can be partially or completely made of wire, which can define any implant body and aperture size and shape as desired. The wire 100 can define a first wire segment 102 and a second wire segment 104 that are shaped to define the bone implant. The first and second wire segments 102 and 104 can be integral and monolithic to form the wire 100. Alternatively, the first and second wire segments 102 and 104 can be separate from each other and defined by two different respective wires. The wire segments 102 and 104 can be defined be a respective single strand of wire or can be defined by multiple strands of wire that can be braided, twisted, or otherwise attached to each other so as to define the respective wire segments 102 and 104. The wire 100 defines a wire outer surface 101 that defines the bone facing surface 52, the opposed upper surface 54, lateral sides 38 and 40, and the at least one inner wall 53.

The at least one inner wall 53 can include a first inner wall 53*a* and a second inner wall 53*b* that faces the first inner wall 53*a* along the lateral direction A. For instance, the first wire segment 102 is shaped to define the first inner wall 53*a*, and the second wire segment 104 is shaped to define the second inner wall 53*b*, such that the first and second inner walls 53*a* and 53*b* define the plurality of bone fixation apertures 56 as detailed below. It should be appreciated that the wire segments 102 and 104 can be defined by a single monolithic wire 100, or can alternatively be defined by two different wires that are disposed adjacent to each other so as to define the wire segments 102 and 104. The wire segments 102 and 104 can define a circular cross-sectional shape such that the inner walls 53*a* and 53*b* can be curved, for instance convex, as they extend along the transverse direction T. The inner walls 53*a* and 53*b* can further be curved as they extend along the longitudinal direction L. Further, first portions 42*a* of the first and second inner walls 53*a* and 53*b* are concave as they extend along the longitudinal direction L so as to define the bone fixation apertures 56, and second portions 42*b* of the first and second inner walls 53*a* and 53*b* adjacent the first portions 42*a* are convex as they extend along the longitudinal direction L so as to define necks 108 that are disposed between adjacent ones of the bone fixation apertures 56.

The bone facing surface 52 and the upper surface 54 can lie in respective planes that are spaced from each other along the transverse direction T and are each defined by the longitudinal direction L and the lateral direction A. While the bone implant 24 can be defined by the first and second wire segments 102 and 104 as illustrated in FIGS. 1A-4C, the bone implant 24 alternatively be defined by a bone plate illustrated in FIG. 5, such that the at least one inner wall 53 can be defined by a single inner wall as described in more detailed below. Unless otherwise indicated, reference herein to the "inner wall 53" can be used to identify at least one inner wall, including reference to the first and second inner walls 53a and 53b, and reference to a single inner wall.

As described above, the bone implant 24 defines the plurality of bone fixation apertures 56 that extend though the implant body 30. For instance, the first and second inner walls 53a and 53b can define each of the plurality of apertures 56 that include a first aperture 56a and a second aperture 56b that is spaced from the first aperture 56a along the longitudinal direction L. The bone implant 24 can include any number of apertures as desired. The first and second apertures 56a and 56b are configured to receive respective ones of the bone fixation element 26 therein. In particular, the bone fixation system 20 can include a plurality of bone fixation elements 26, including a first bone fixation element 26a that is configured to be inserted into the first bone fixation aperture 56a and a second bone fixation element 26b that is configured to be inserted into the second bone fixation aperture 56b. For instance, the bone implant 24 can be positioned such that the first bone fixation aperture 56a is aligned with the first bone fragment 27a, and the second bone fixation aperture 56b is aligned with the second bone fragment 27b. Thus, the bone gap 27c is positioned between the first and second bone fixation apertures 56a and 56b. The first bone fixation element 26a can be inserted into the first bone fixation aperture 56a and into the first bone fragment 27a so as to secure the bone implant 24 to the first bone fragment 27a, and the second bone fixation element 26b can be inserted into the second bone fixation aperture 56b and into the second bone fragment 27b so as to secure the bone implant 24 to the second bone fragment 27b. Thus, the bone implant 24 can be secured to the fixation site 28 and so as to promote fusion of the first bone fragment 27a to the second bone fragment 27b.

As described above, the first and second wire segments 102 and 104 define a plurality of necks 108 that can define one or both boundaries of the bone fixation apertures 56 along the longitudinal direction L. The necks 108 can be defined by respective locations where the first and second inner walls 53a and 53b are closest together at the respective second portions 42b. For instance, the locations of the necks 108 can bifurcate the second portions 42b along the longitudinal direction L. In accordance with one embodiment, the locations of the necks 108 define respective intersection points where the first inner wall 53a and the second inner wall 53b abut each other. The first and second inner walls 53a and 53b can further be secured, for instance soldered, welded, or otherwise attached, to each other at the locations of the necks 108. The first wire segment 102 extends along the longitudinal direction L between adjacent necks 108 to define the first inner wall 53a, and the second wire segment 104 extends along the longitudinal direction L between the adjacent necks 108 to define the second inner wall 53b. The first and second wire segments 102 and 104 extend along the longitudinal direction L to define spaced apart longitudinal ends of the bone fixation apertures 56 defined by a pair of adjacent necks 108. Thus, each bone fixation aperture 56 extends between a first one of the longitudinal ends and second one of the longitudinal ends that is spaced from the first one of the longitudinal ends along the central implant axis 32 between adjacent locations of the necks 108. The locations of the necks 108 can be disposed on the central axis 32.

With continuing reference to FIGS. 2A-2C, the inner wall 53 of the implant body 30 is threaded along the respective bone fixation apertures 56. Thus, it can be said that at least a portion of the inner wall 53, including at least a portion of the first inner wall 53a and at least a portion of the second inner wall 53b, is threaded. For instance, the first and second inner walls 53a and 53b defines respective threads 58 that can be helically arranged and configured to threadedly mate with respective threads of the bone fixation element 26 when the bone fixation element 26 is inserted into the respective bone fixation aperture 56. The threads of the first inner wall 53a, when continued to the threads of the second inner wall 53b opposite the threads of the first inner wall 53 along the lateral direction A, can define a helical path. Thus, the threads 58 can be referred to as internal threads. The threads 58 can be disposed at a respective first threaded region 60 defined by the first wire segment 102 and a respective second threaded region 62 defined by the second wire segment 104. Thus, the first inner wall 53a defines the first threaded region 60 and the second inner wall 53b defines the second threaded region 62. The first threaded region 60 extends along the first wire segment 102 from a respective proximal end to a respective distal end that is spaced from the proximal end in the distal direction. Similarly, the second threaded region 62 extends along the second wire segment 104 from a respective proximal end to a respective distal end that is spaced from the proximal end in the distal direction. Further, the first and second threaded regions 60 and 62 extend along a portion of the inner walls 53a and 53b, respectively, along the longitudinal direction. For instance, the threads 58 extend along at least part of the first portions 42a of the respective first and second inner walls 53a and 53b. For instance, the threads 58 can extend along both the first and second portions 42a and 42b of the respective first and second inner walls 53a and 53b from a first one of the necks 108 to an adjacent one of the necks 108 if desired.

Referring now to FIG. 2C in particular, the inner wall 53 can combine so as to define a single thread 58 that extends about at least a portion of the perimeter of each bone fixation aperture 56, or can alternatively define multiple intertwined threads that define what is known as a multiple start screw. Thus, it can be said that the inner wall 53 defines at least one thread 58. In accordance with one embodiment, the at least one thread 58 of the first and second inner walls 53a and 53b can be continuous with each other along a helical path.

Each at least one thread 58 includes a first surface 72a and an opposed second surface 72b. At least one or both of the first and second surfaces 72a and 72b converges toward the other of the first and second surfaces 72a and 72b as the first and second surfaces 72a and 72b extend toward the central aperture axis 59. In particular, each of the first and second surfaces 72a and 72b converge from a root 72c of the thread 58 to a crest 72d of the thread 58. The implant body 30, and thus the bone implant 24, defines a major diameter D1 that is defined by the root 72c and extends along a direction perpendicular to the central aperture axis 59 and intersects the central aperture axis 59. The implant body 30, and thus the bone implant 24, defines a minor diameter d1 that is defined by the crest 72d and extends along a direction perpendicular to the central aperture axis 59 and intersects the central aperture axis 59.

The first surface 72a is spaced from the second surface 72b in the proximal direction. Thus, the second surface 72b is spaced from the first surface in the distal direction. The first surface 72a can be referred to as a leading surface with respect to insertion of the bone fixation element 26 into the respective bone fixation aperture 56, and the second surface 72*b* can be referred to as a trailing surface with respect to insertion of the bone fixation element 26 into the respective bone fixation aperture 56. It should be appreciated, of course, that if the bone fixation element 26 is removed from the bone fixation aperture 56, the second surface 72*b* becomes the leading surface and the first surface 72*a* becomes the trailing surface. In accordance with the illustrated embodiment, each of the first and second surfaces 72*a* and 72*b*, in cross-section through a plane that is partially defined by the central aperture axis 59, defines a first angle less than 90 degrees with respect to a reference plane that is oriented normal with respect to the central aperture axis 59. For instance, the first and second surfaces 72*a* and 72*b*, in said cross section, can define equal and opposite first angles with respect to the reference plane.

In accordance with the illustrated embodiment, the inner walls 53*a* and 53*b* can define as many intertwined screw threads 58 as desired, for instance one, two, three, or more. Thus, the inner walls 53*a* and 53*b* define a lead L1, which is defined by the axial advance of the bone fixation element 26 along the central aperture axis 59 when threadedly mated with the at least one thread 58 and rotated one complete 360 degree revolution. The inner wall 53 further defines a pitch P1, that is the axial distance along the central aperture axis 59 between adjacent ones of the crests 72*d*, which can be defined by the same thread 58, for instance if the inner surfaces 53 defines a single thread, or can be defined by different threads 58, for instance if the inner wall 53 defines multiple intertwined threads 58. Thus, the lead L1 is a multiple of the pitch P1 by the number of intertwined threads 58 defined by the inner wall 53. When the inner wall 53 defines a single thread 58, the multiple is one, and the lead L1 is equal to the pitch P1.

Referring now also to FIGS. 3A-3B, the bone fixation element 26 is elongate along a central axis 31 that can extend along the transverse direction T, and defines a proximal end 29*a* and a distal end 29*b* that is spaced from the proximal end 29*a* in a distal direction along the central axis 31. Thus, the proximal end 29*a* is spaced from the distal end 29*b* in a proximal direction. The central axis 31 is coaxial with the central aperture axis 59 when the bone fixation element 26 is disposed in the bone fixation aperture 56. The bone fixation element 26 can be an anchor, rivet, bone pin or screw configured for securement to the fixation site 28.

The bone fixation element 26 can include a head 80 and a shaft 82 that extends in the distal direction with respect to the head 80. The shaft 82 can define a length in the transverse direction T that is greater than the length of the head 80 in the transverse direction T. For instance, the shaft 82 can extend directly from the head 80, or the bone fixation element 26 can include a necked region 83 that extends between the head 80 and the shaft 82. Thus, the proximal end 29*a* of the bone fixation element 26 can be defined by the head 80, and the distal end 29*b* of the bone fixation element 26 can be defined by the shaft 82. At least a portion of the shaft 82 can be threaded along the transverse direction T, and can define at least one external thread, such as a thread 84. The thread 84 can be helical and can extend from a root 85*a* to a crest 85*b* along a direction away from the central axis 31. The shaft 82 thus defines major diameter D2 that is defined by the crest 85*b* and extends along a direction perpendicular to the central axis 31 and intersects the central axis 31. The shaft 82 can further define a minor diameter d2 that is defined by the root 85*a* and extends along a direction perpendicular to the central axis 31 and intersects the central axis 31. The thread 84 can be helical, and can define a pitch P2 and a lead L2. The at least one thread 84 can be a single thread, such that the lead L2 is equal to the pitch P2. Alternatively the shaft 82 can define multiple intertwined threads such that the lead L2 is a multiple of the pitch P2 as described above with respect to the thread 58 of the bone implant 24.

The minor diameter d1 of the at least one thread 58 of the bone implant 24 can be greater than the major diameter D2 of the at least one thread 84 of the shaft 82, such that the shaft 82 can be advanced through the bone fixation aperture 56 along the distal direction without rotating the bone fixation element 26 with respect to the bone implant 24, and without causing at least one thread 84 to interfere with the at least one thread 58. Accordingly, during operation, the shaft 82 can be advanced through one of the bone fixation apertures 56, until the shaft 82 contacts the fixation site 28. The bone fixation element 26, including the shaft 82, can be rotatably driven into the underlying fixation site 28, such that the thread 84 purchases with the fixation site 28, for instance the bone 27, thereby securing the shaft 82 to the fixation site 28. The thread 84 of the shaft 82 at the distal end 29*b* can define one or more cutting flutes such that the bone fixation element 26 is configured as a self-tapping screw. Alternatively, the at least one thread 84 can be devoid of cutting flutes, such that the bone fixation element 26 defines a standard screw whereby the threads 84 intermesh with the bone 27 through a pilot hole that has been pre-drilled into the bone 27, thereby securing the shaft 82 to the fixation site 28.

With continuing reference to FIGS. 3A-B, the head 80 can also be threaded along the transverse direction T, and can define at least one thread 88, which can be configured as an external thread. The at least one thread 88 can include a single thread or a plurality of intertwined threads as described above with respect to the inner wall 53 of the bone implant 24. Each of the threads 88 includes a first surface 89*a* and an opposed second surface 89*b*. At least one or both of the first and second surfaces 89*a* and 89*b* converges toward the other of the first and second surfaces 89*a* and 89*b* as the first and second surfaces 89*a* and 89*b* extend away from the central axis 31. In particular, each of the first and second surfaces 89*a* and 89*b* converge from a root 89*c* of the thread 88 to a crest 89*d* of the thread 88. The head 80 defines a major diameter D3 that is defined by the crest 89*d* and extends along a direction perpendicular to the central axis 31 and intersects the central axis 31. The head 80 can further defines a minor diameter d3 that is defined by the root 89*c* and extends along a direction perpendicular to the central axis 31 and intersects the central axis 31.

The necked region 83 defines an outer diameter D4 that is less than the major diameter D3 of the head 80. Both the outer diameter D4 of the necked region 83 and the major diameter D2 of the shaft 82 are less than the minor diameter d1 of the bone implant 24 such that both the shaft 82 and the necked region 83 can advance through the at least one bone fixation aperture 56 without interfering with the respective at least one thread 58. The outer diameter D4 of the necked region 83 can be less than one or both of the major diameter D2 and the minor diameter d2 of the shaft 82, greater than one or both of the major diameter D2 and the minor diameter d2 of the shaft 82, or equal to one or both of the major diameter D2 and the minor diameter d2 of the shaft 82 as desired.

The major diameter D3 of the head 80 is greater than the major diameter D2 of the shaft 82 and the outer diameter D4 of the necked region 83. For instance, the major diameter D3 of the head 80 is less than the major diameter D1 of the bone implant 24 and greater than the minor diameter d1 of the bone implant 24. Further, the minor diameter d3 of the head 80 is less than the minor diameter d1 of the bone implant 24. Thus, when the central axis 31 of the bone anchor 24 is aligned with the central aperture axis 59, and the distal end of the at least one thread 88 contacts the at least one thread 58 of the inner wall 53, rotation of the bone anchor 24 in a first direction of rotation causes the at least one thread 88 to threadedly mate with the at least one thread 58 of the bone implant 24, which advances the bone fixation element 26 along the distal direction with respect to the bone implant 24, thereby advancing the head 80 in the respective bone fixation aperture 56 in the distal direction. It is further appreciated that rotation of the bone fixation element 26 in the first direction can further drive the shaft 82 into the underlying bone 27. It is recognized that rotation of the bone fixation element 26 in a second direction of rotation that is opposite the first direction of rotation can cause the head 80 to retract from the respective bone fixation aperture 56 along the proximal direction until the head 80 is removed from the bone fixation aperture 56. Furthermore, rotation of the bone fixation element 26 in the second direction of rotation can cause the shaft 82 to retract from the underlying bone 27 along the proximal direction until the shaft 82 is removed from the underlying bone 27.

The bone fixation element 26 can further define an instrument engagement member that is configured to mate with a driving instrument so as to receive a drive force that causes the bone fixation element 26 to rotate in one of the first and second directions of rotation. The tool engagement member can, for instance, be configured as a socket 93 that extends into the head 80 in the distal direction along the central axis 31. The socket 93 can have any suitable shape configured to receive the driving instrument. For instance, the socket 93 can be a square, hex, cross, slot, flat, star, hexalobular, or any other suitable shape to receive a tool. Further, the bone fixation element 26 can be cannualated from the socket 93 through the head 80 and through the shaft 82 along the central axis 31, and further can include one or more bores that extend through the shaft 82 to the cannulation. The cannulation and the bores can be configured to receive a temporary guidewire, such as a Kirschner wire that can be temporarily driven into the fixation site 28, such that the guidewire guides the bone fixation element 26 to the fixation site 28 during fixation of the bone fixation element 26 into the fixation site 28. The guidewire can then be removed from the fixation site 28 and the cannulation. Further, the bores can be configured to receive for receiving additional fixation elements therethrough, such as a temporary guidewire or Kirschner wire, or an additional screw that can be inserted through the socket 93 and the transverse bore to secure to the bone 27 or the implant. The bores can also allow for bone ingrowth as wel.

The first surface 89a is spaced from the second surface 89b in the proximal direction. Thus, the second surface 89b is spaced from the first surface 89a in the distal direction. The second surface 89b can be referred to as a leading surface with respect to insertion of the bone fixation element 26 into the respective bone fixation aperture 56, and the first surface 89a can be referred to as a trailing surface with respect to insertion of the bone fixation element 26 into the respective bone fixation aperture 56. Thus, the leading surface of the at least one thread 88 of the head 80 faces the leading surface of the at least one thread 58 of the bone implant 24 as the head 80 threadedly engages the bone implant 24 in the bone fixation aperture 56. It should be appreciated, of course, that if the bone fixation element 26 is removed from the bone fixation aperture 56, the first surface 89a becomes the leading surface and the second surface 89b becomes the trailing surface. In accordance with the illustrated embodiment, each of the first and second surfaces 89a and 89b, in cross-section through a plane that is partially defined by the central axis 31, defines a second angle less than 90 degrees with respect to a reference plane that is oriented normal with respect to the central axis 31. For instance, the first and second surfaces 89a and 89b, in said cross section, can define equal and opposite second angles with respect to the reference plane. The second angle defined by the at least one thread 88 is substantially equal to the first angle defined by the at least one thread 58 of the bone implant 24.

In accordance with the illustrated embodiment, the outer surface of the head 80 can define as many intertwined screw threads 88 as desired, for instance one, two, three, or more. Thus, the head 80 defines a lead L3, which is defined by the axial advance of the bone fixation element 26 along the central aperture axis 59 when threadedly mated with the at least one thread 58 and rotated one complete 360 degree revolution. The head 80 further defines a pitch P3, that is the axial distance along the central axis 31 between adjacent ones of the crests 89d, which can be defined by the same thread 88, for instance if the head 80 defines a single thread, or can be defined by different threads 88, for instance if the head 80 defines multiple intertwined threads 88. Thus, the lead L3 is a multiple of the pitch P3 by the number of intertwined threads 88 defined by the head 80. When the head 80 define a single thread 88, the multiple is one, and the lead L3 is equal to the pitch P3. The lead L3 is substantially equal to the lead L1 of the bone implant 24, and the pitch P3 is substantially equal to the Pitch P1 of the bone implant 24. Further, the leads L1 and L2 of the head 80 and the bone implant 24, respectively, can be substantially equal to the lead L3 of the shaft 82. Accordingly, the shaft 82 advances into the bone 27 in the distal direction at the same rate (e.g., distance per revolution of the bone fixation element 26 relative to the bone 27) as the rate that the head 80 advances in the bone fixation aperture 56 in the distal direction (e.g., distance per revolution of the bone fixation element 26 relative to the bone implant 24). The pitches P1 and P2 of the head 80 and bone implant 24, respectively, can further be substantially equal to the pitch L3 of the shaft 82 when, for instance, the at least one thread 58 of the respective bone fixation aperture 56, the at least one thread 88 of the head 80, and the at least one thread 84 of the shaft 82 define the same number of threads.

The major diameter D1 of the at least one thread 58 of the bone implant 24 can be greater than the major diameter D2 of the at least one thread 84 of the shaft 82, such that the shaft 82 can be advanced through the bone fixation aperture 56 along the distal direction without rotating the bone fixation element 26 with respect to the bone implant 24, and without causing at least one thread 84 to interfere with the at least one thread 58. Accordingly, during operation, the shaft 82 can be advanced through one of the bone fixation apertures 56, until the shaft 82 contacts the fixation site 28. The bone fixation element 26, including the shaft 82, can be rotatably driven into the underlying fixation site 28, such that the thread 84 purchases with the fixation site 28, for instance the bone 27, thereby securing the shaft 82 to the fixation site 28. The thread 84 of the shaft 82 at the distal end 29b can define one or more cutting flutes such that the bone fixation element 26 is configured as a self-tapping screw. Alternatively, the at least one thread 84 can be devoid of cutting flutes, such that the bone fixation element 26 defines a standard screw whereby the threads 84 intermesh with the bone 27 through a pilot hole that has been pre-drilled into the bone 27, thereby securing the shaft 82 to the fixation site 28.

With continuing reference to FIGS. 3A-B, the head 80 defines a ridge 92 that is positioned adjacent the at least one thread 88 of the head 80 so as to be spaced from the at least one thread 88 along the proximal direction. Thus, the at least one thread 88 can be spaced from the ridge 92 along the distal direction. For instance, an entirety of the at least one thread 88 can be spaced from the ridge 92 along the distal direction. Alternatively, the at least one thread 88 can be partially defined by the ridge 92, such that a portion of the at least one thread 88 extends distal with respect to the ridge 92. The ridge 92 defines an outer cross-sectional dimension D5 along a plane defined by the longitudinal direction L and the lateral direction A. The outer cross-sectional dimension D5 is greater than the major diameter D3 of the head 80 and further greater than at least the minor diameter d1 of the bone implant 24. Further, the outer cross-sectional dimension D5 can be greater than the major diameter D1 of the bone implant 24. The ridge 92 can be circular in shape in a cross-section with respect to a plane that extends along the longitudinal and lateral directions, such that the outer cross-sectional dimension D5 is a diameter. Alternatively, the ridge 92 can define any suitable alternative shape in said cross-section as desired. The ridge 92 defines a stop surface that is aligned with a portion of the bone implant 24 along the transverse direction T. Accordingly, as will be described in more detail below, the ridge 92 is configured to abut the bone implant 24 when the head 80 threadedly engages the bone anchor 24 in the respective fixation aperture 56. The ridge 92 can be continuous about the perimeter of the head 80 or segmented about the perimeter of the head 80.

Referring now to FIGS. 4A-4C, during operation the bone implant 24 is positioned at a location as desired with respect to the underlying bone 27 such that the bone facing surface 52 faces the underlying fixation site 28 or bone 27, and the upper surface 54 faces away from the underlying fixation site 28 or bone 27 (see also FIG. 1A). For instance, the location can be such that the bone implant 24 is positioned against the underlying bone 27 or such that the bone implant 24 is spaced from the underlying bone as desired. The bone implant is positioned such that the bone gap is disposed between first and second ones of the bone fixation apertures 56 in the manner described above. A first bone fixation element 26 is driven through the first one of the bone fixation apertures 56 and into the first fixation site 28a, and a second bone fixation element 26 is driven through the second one of the bone fixation apertures 56 and into the second fixation site 28b. In particular, as each bone fixation element 26 is driven through the respective bone fixation aperture 56 an into the underlying fixation site 28 and rotated with respect to both the fixation site 28 and the bone implant 24, the threaded shaft 82 can be threadedly driven into the underlying bone 27 in the manner described above. The bone fixation element 26 is driven into the underlying bone 27 until the at least one thread 88 of the head 80 begins to threadedly mate with the at least one thread 58 of the bone implant 24. Continued rotation of the bone fixation element 26 with respect to both the fixation site 28 and the bone implant 24 causes the at least one thread 88 to further threadedly mate with the at least one thread 58 of the bone implant 24 as the head 90 advances in the distal direction in the bone fixation aperture 56.

As illustrated in FIGS. 4B-4C because the major diameter D3 of the head 80 is less than the major diameter D1 of the bone implant 24, a gap 90 can be defined between the at least one thread 88 of the head 80 and the at least one thread 58 of the bone implant 24 along a line that extends in the transverse direction T, and thus parallel to the central axis 31 and the central aperture axis 59. For instance, the gap 90 can be defined between the first surface 89a of the head 80 and the at least one thread 58, between the second surface 89b and the at least one thread 58, or a first portion of the gap 90 can be defined between the first surface 89a and the at least one thread 58, and a second portion of the gap 90 can be defined between the second surface 89b and the at least one thread 58. For instance, the gap 90 or the first portion of the gap 90 that is defined between the first surface 89a and the at least one thread 58 can in particular be defined between the first surface 89a and the second surface 72b. The gap 90 or the second portion of the gap 90 that is defined between the second surface 89b and the at least one thread can in particular be defined between the second surface 89b and the first surface 72a. It can further be said that the gap 90 can be defined between the first surface 89a of the head 80 and the inner wall 53, between the second surface 89b and the inner wall 53, or a first portion of the gap 90 can be defined between the first surface 89a and the inner wall 53, and a second portion of the gap 90 can be defined between the second surface 89b and the inner wall 53.

With further reference to FIGS. 1B-1C and FIGS. 4A-4C, the shaft 82 of the fixation element 26 is driven through the respective bone fixation aperture 56 along the distal direction, and can be rotated in the first direction of rotation, thereby causing the at least one thread 84 to threadedly purchase with the first fixation site 28a, as the shaft 82 is driven into the first fixation site 28a, which can be defined by the underlying bone 27. As the shaft 82 is advanced in the first fixation site 28a, the at least one thread 88 of the head 80 threadedly mates with the at least one thread 58 in the respective bone fixation aperture 56 of the bone implant 24 as illustrated in FIG. 4A. Continued rotation of the bone fixation element 26 in the first direction causes the ridge 92 to move distally with respect to the bone implant 24 until the ridge 92, and in particular the stop surface of the ridge 92, contacts the bone implant 24 at a contact location 95, as illustrated in FIGS. 4B-4C. The contact location 95 can be defined by the inner wall 53. It should be appreciated that at least a portion of the bone implant 24, for instance at least a portion of the inner wall 53, is disposed between the ridge 92 and a threaded region of the head 80, which can be defined by the at least one thread 88.

As described above, at least a portion of the gap 90 can be disposed between the first surface 89a and the at least one thread 58 of the bone implant 24, for instance the second surface 72b of the at least one thread 58. Thus, referring to FIGS. 4D-4E, the bone implant 24 can be prevented from jiggling with respect to the bone fixation element 26 along the transverse direction T, both in the proximal direction and in the distal direction, due to clearance provided by the gap 90, also known as backlash. For instance, further rotation of the bone fixation element 26 in the first direction of rotation causes the ridge 92, and in particular the stop surface of the ridge 92, to bear against the implant body 30 at the contact location 95, thereby driving the bone implant 24 in the distal direction with respect to the at least one thread 88 until the at least one thread 58 contacts the first surface 89a. Thus, implant body 30, and in particular the inner wall 53, and thus the bone implant 24, is compressed between the stop surface, for instance the ridge 92, and the at least one thread 88, for instance the leading surface of the at least one thread. In particular, the proximal end of the implant body 30 bears against the stop surface, which can be defined by the ridge 92, and the at least one thread 58 bears against the at least one thread 88. The implant body 30 is compressed between the ridge 92 and the at least one thread 88 while the at least one thread 88 is threadedly mated with the at least one thread 58 of the bone implant 24. Accordingly, an entirety of the gap 90 is disposed between the second surface 89b and the at least one thread 58, for instance the first surface 72a of the at least one thread 58. Accordingly, contact between the ridge 92 and the bone implant 24 prevents the bone implant 24 from moving in the proximal direction with respect to the bone fixation element 26. Furthermore, contact between the first surface 89a of the at least one thread 88 of the head 80 and the second surface 72b of the at least one thread 58 of the bone implant 24 prevents the bone implant 24 from moving in the distal direction with respect to the bone fixation element 26. Thus, relative movement is prevented between the bone fixation element 26 and the bone implant 24 along the transverse direction.

The ridge 92 can define a height along the transverse direction T from the contact location 95 to the proximal-most surface of the ridge 92 that is no greater than the height of the bone implant from the contact location 95 to the proximal-most end of the upper surface 54. For instance, the proximal-most end of the upper surface 54 can lie within a first plane that is defined by the lateral direction A and the longitudinal direction L. The contact location 95 can lie in a reference plane that is defined by the lateral direction and the longitudinal direction L. The reference plane is spaced from the first plane along the transverse direction T a first height. The proximal-most end of the ridge 92 can lie within a second plane that is defined by the lateral direction A and the longitudinal direction L. The third plane is spaced from the reference plane along the transverse direction T a second height that is no greater than the first height. For instance, the second height of the ridge 92 can be less than the first height. Accordingly, when the ridge 92 is in contact with the bone implant 24 at the contact location 95, the ridge 92 does not project out with respect to the proximal-most end of the upper surface 54 along the proximal direction.

Further, the ridge 92 can defines a height along the transverse direction T from the contact location 95 to the distal-most surface of the head 80 that is no greater than the height of the bone implant 24 from the contact location 95 to the distal-most end of the bone facing surface 52. For instance, the distal-most end of the upper surface 54 can lie within a third plane that is defined by the lateral direction A and the longitudinal direction L. The third plane is spaced from the reference plane in the transverse direction T a third height. The distal-most end of the ridge 92 can lie within a fourth plane that is defined by the lateral direction A and the longitudinal direction L. The fourth plane is spaced from the reference plane so as to define a fourth height that is no greater than the third height. For instance, the fourth height of the ridge 92 can be less than the third height. Accordingly, when the ridge 92 is in contact with the bone implant 24 at the contact location 95, the ridge 92 does not project out with respect to the distal-most end of the bone facing surface 52 along the distal direction. Because the head 80 does not project out with respect to the bone implant 24 along the transverse direction T in accordance with one embodiment, the head 80 does not irritate soft tissue that is in close proximity to the bone implant 24.

In accordance with one embodiment, because the lead L1 of the bone implant 24 and the lead L3 of the head 80 are substantially equal to the lead L2 of the shaft 82, rotation of the bone anchor 24 in the first direction of rotation does not cause the bone implant 24 to move substantially toward or away from the underlying bone 27 as the shaft 82 threadedly purchases with the underlying bone at the respective fixation site 28 while the head 80 threadedly mates with the bone implant 24 in the respective fixation aperture 56. Alternatively, it is appreciated that the lead L2 of the shaft 82 can be different than each of the lead L1 of the bone implant 24 and the lead L3 of the head 80. Accordingly, the bone implant 24 can move with respect to underlying bone 27 along the transverse direction T as the shaft 82 threadedly purchases with the underlying bone at the respective fixation site 28 while the head 80 threadedly mates with the bone implant 24 in the respective fixation aperture 56. For instance, the lead L2 of the shaft 82 can be greater than each of the lead L1 of the bone implant 24 and the lead L3 of the head 80. Accordingly, the shaft 82 can advance in the fixation site in the distal direction during rotation of the bone fixation element at a first rate that is greater than a second rate at which the head 80 advances in the distal direction in the bone fixation aperture 56. Thus, the bone implant 24 can move toward the underlying bone 27 in the distal direction as the shaft 82 threadedly purchases with the underlying bone at the respective fixation site 28 while the head 80 threadedly mates with the bone implant 24 in the respective fixation aperture 56. Thus, the bone implant 24 can be placed adjacent the underlying bone 27, such that the bone implant 24 is compressed against the underlying bone 27 as the shaft 82 threadedly purchases with the underlying bone 27 at the respective fixation site 28 while the head 80 threadedly mates with the bone implant 24 in the respective fixation aperture 56. Alternatively still, the lead L2 of the shaft 82 can be less than each of the lead L1 of the bone implant 24 and the lead L3 of the head 80. Accordingly, the bone implant 24 can move away from the underlying bone 27 along the transverse direction T as the shaft 82 threadedly purchases with the underlying bone at the respective fixation site 28 while the head 80 threadedly mates with the bone implant 24 in the respective fixation aperture 56.

Referring again to FIG. 1C, at least one first bone fixation element 26a is secured to both the first fixation site 28a and the bone implant 24 in a respective at least one first bone fixation aperture 56a as described above, and at least one second bone fixation element 26b can be secured to both the second fixation site 28b and the bone implant 24 in a respective at least one second bone fixation aperture 56b. The bone fixation system can include as many first bone fixation elements 26a as desired, and as many second bone fixation elements 26b as desired.

It should thus be appreciated that coupling the bone fixation elements 26 to the bone implant 24 and the underlying bone 27 provides 1) angularly stability between the bone fixation element 26 and the bone implant 24, and 2) prevents relative movement between the bone fixation element 26 and the bone implant 24 along the transverse direction T. For instance, when a plurality of bone fixation elements 26 are coupled to bone implant 24 and secured to a corresponding fixation site 28, angularly stable fixation is achieved because the bone implant 24 forms a stable bridging structure with the bone fixation elements 26 that spans the fracture location FL. Further, the bone fixation element 26 can be coupled to the bone implant 24 such that at least a portion of the bone implant 24, for instance a portion of the inner wall 53, is captured between 1) a stop surface of the bone fixation element 26, for instance the head 80, and 2) a threaded region of the head 80. For instance, the stop surface can be defined by the ridge 92, and the threaded region can be disposed distal from the ridge 92, and can be defined by the at least one thread 88 of the head 80.

Figure 5:
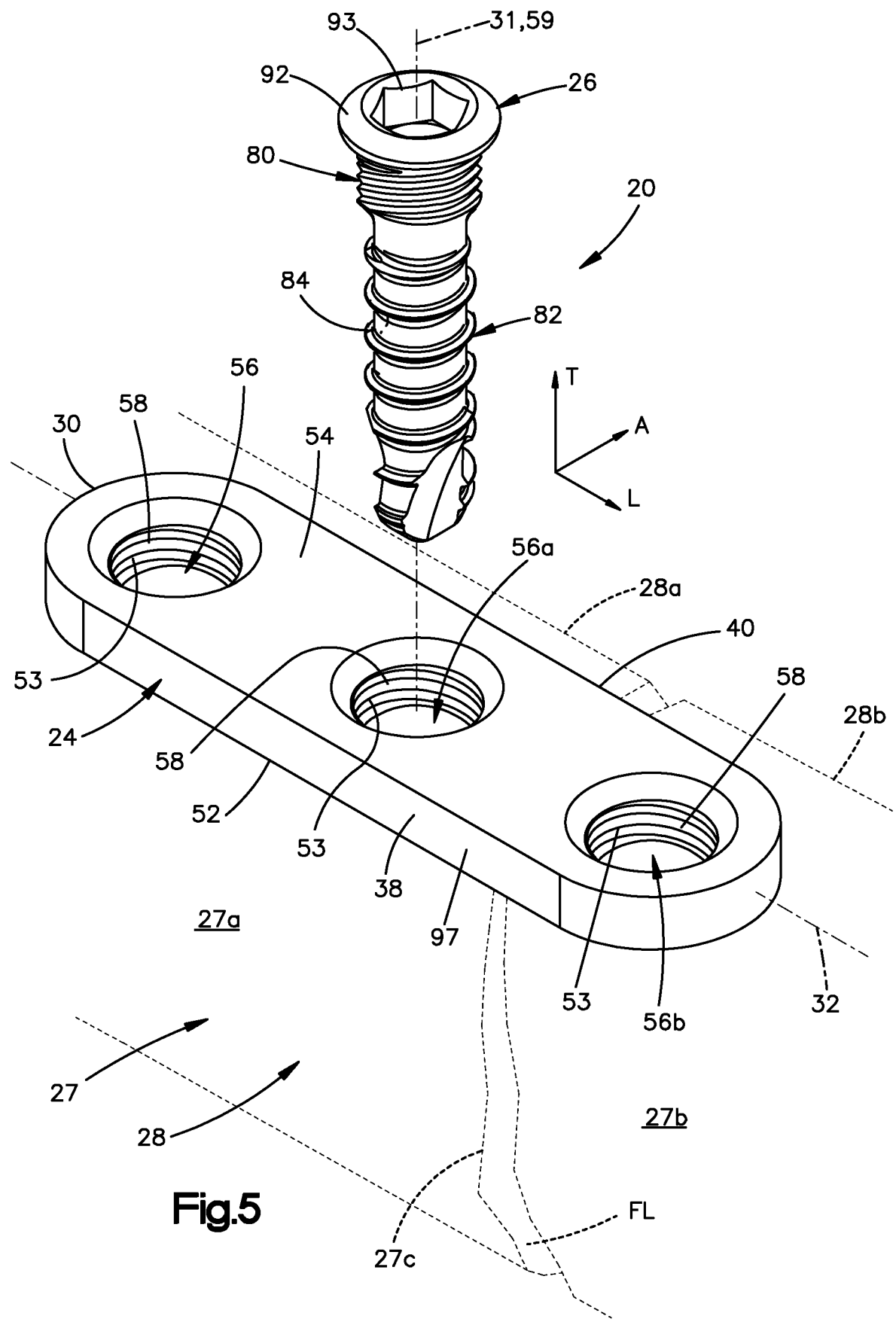
FIG. 5 is a perspective view of the bone fixation system as illustrated in FIG. 1A, but showing the bone implant constructed in accordance with an alternative embodiment.

Referring now to FIG. 5, it should be appreciated that, unless otherwise indicated, the bone implant 24 can be constructed in accordance with any suitable alternative embodiment. For instance, while the bone implant 24 can be defined by the first and second wire segments 102 and 104 as described above, the bone implant 24 can alternatively be defined by a bone plate 97 that defines the implant body 30. The implant body 30, and thus the bone plate 97, defines the bone facing surface 52 and the upper surface 54 as described above, and further defines a plurality of inner surfaces 53 that define respective bone fixation apertures 56 that extend through the implant body 30 from the upper surface 54 to the bone facing surface 52. At least a portion of the inner wall 53 defines the at least one thread 58 in the manner described above, such that the at least one thread 88 of the head 80 of the bone fixation element 26 can be threadedly secured to the at least one thread 58 of the bone implant 24 in the manner described above.

The bone fixation system 20 as constructed herein can be formed using any suitable biocompatible materials or combination of the materials. For instance, the bone implant 24 can be formed of metallic materials such as cobalt chromium molybdenum (CoCrMo), stainless steel, titanium, titanium alloys, magnesium, glass metals, ceramic materials, and polymeric materials include plastics, fiber reinforced plastics, polymeric materials that include polyetheretherketone (PEEK), polyetherketoneketone (PEKK), and bioresorbable materials or shape memory materials. In one embodiment, the bone implant 24 can be formed of a combination of polymeric and metallic materials. For instance, the bone implant 24 can be formed of polymeric wire segments, metallic wire segments, or a combination of polymeric and metallic wire segments. The bone implant 24 may be coated an antibacterial coating, drug-eluting coating, or surface modifier such as a carbon diamond coating. In another example, the bone implant 24 may be chemically processed using, for example, anodization, electropolishing, chemical vapor deposition, plasma treatments, or any process to modify or enhance bone implant surface characteristics. The bone fixation elements 26 can also be formed of formed of metallic materials such as cobalt chromium molybdenum (CoCrMo), stainless steel, titanium, titanium alloys, nitinol and Gummetal®, magnesium, glass metals, ceramic materials, and polymeric materials include plastics, fiber reinforced plastics, polymeric materials that include polyetheretherketone (PEEK), polyetherketoneketone (PEKK), and bioresorbable materials or shape memory materials. The bone fixation elements 26 can also be metallic or formed of metallic alloys, such as titanium. The bone fixation element 26 can also be formed of a combination of polymeric and metallic materials. For instance, the bone fixation elements 26 can have a polymeric head and metallic shaft. The bone fixation elements 26 may be coated an antibacterial coating, drug-eluting coating, or surface modifier such as a carbon diamond coating. In another example, the bone fixation elements 26 may be chemically processed using, for example, anodization, electropolishing, chemical vapor deposition, plasma treatments, or any process to modify or enhance bone fixation element surface characteristics.

Figure 6A:
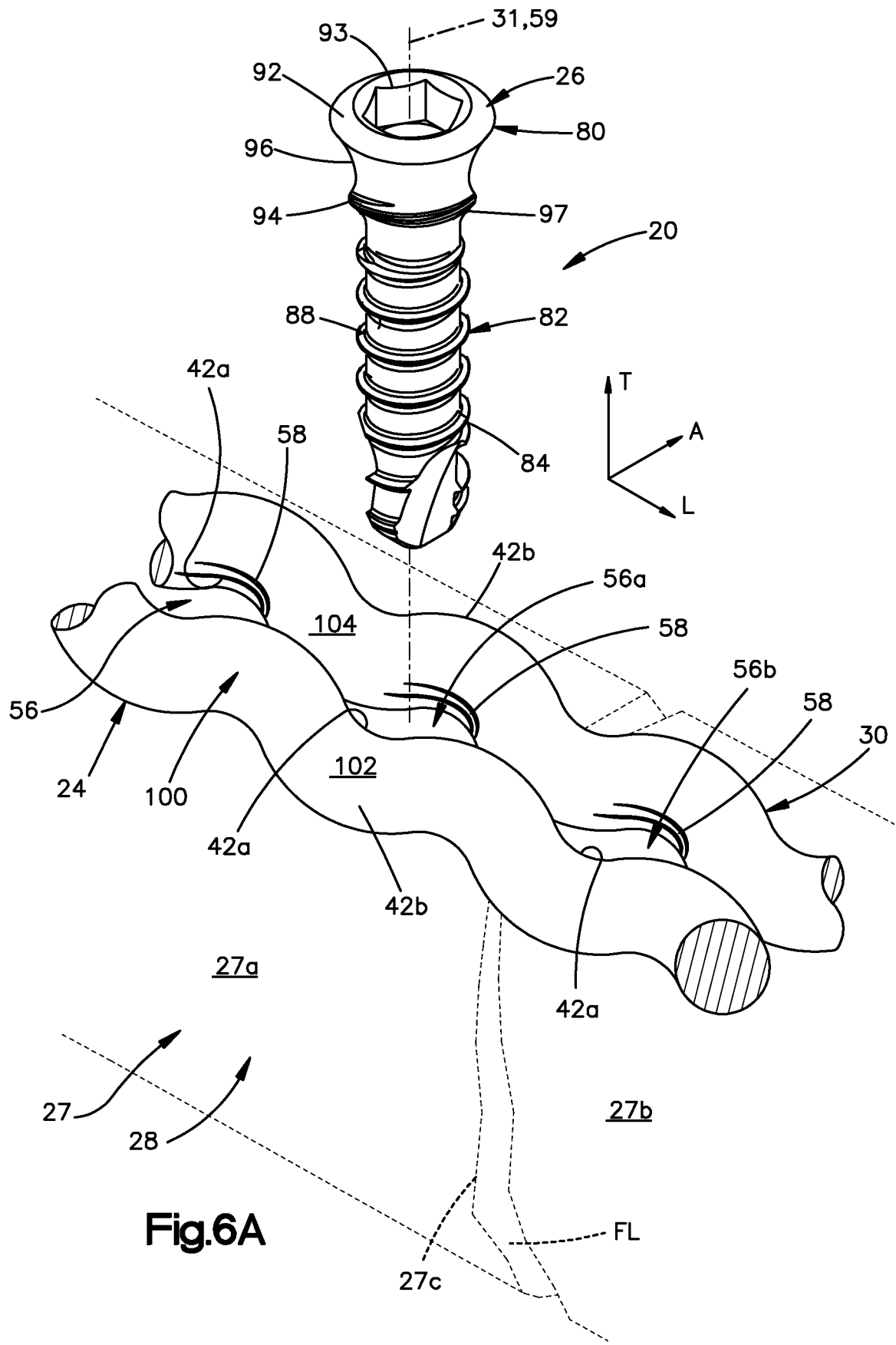
FIG. 6A is an exploded perspective view of the bone fixation system as illustrated in FIG. 1B, but showing the bone fixation element constructed in accordance with another embodiment.
Figure 6B:
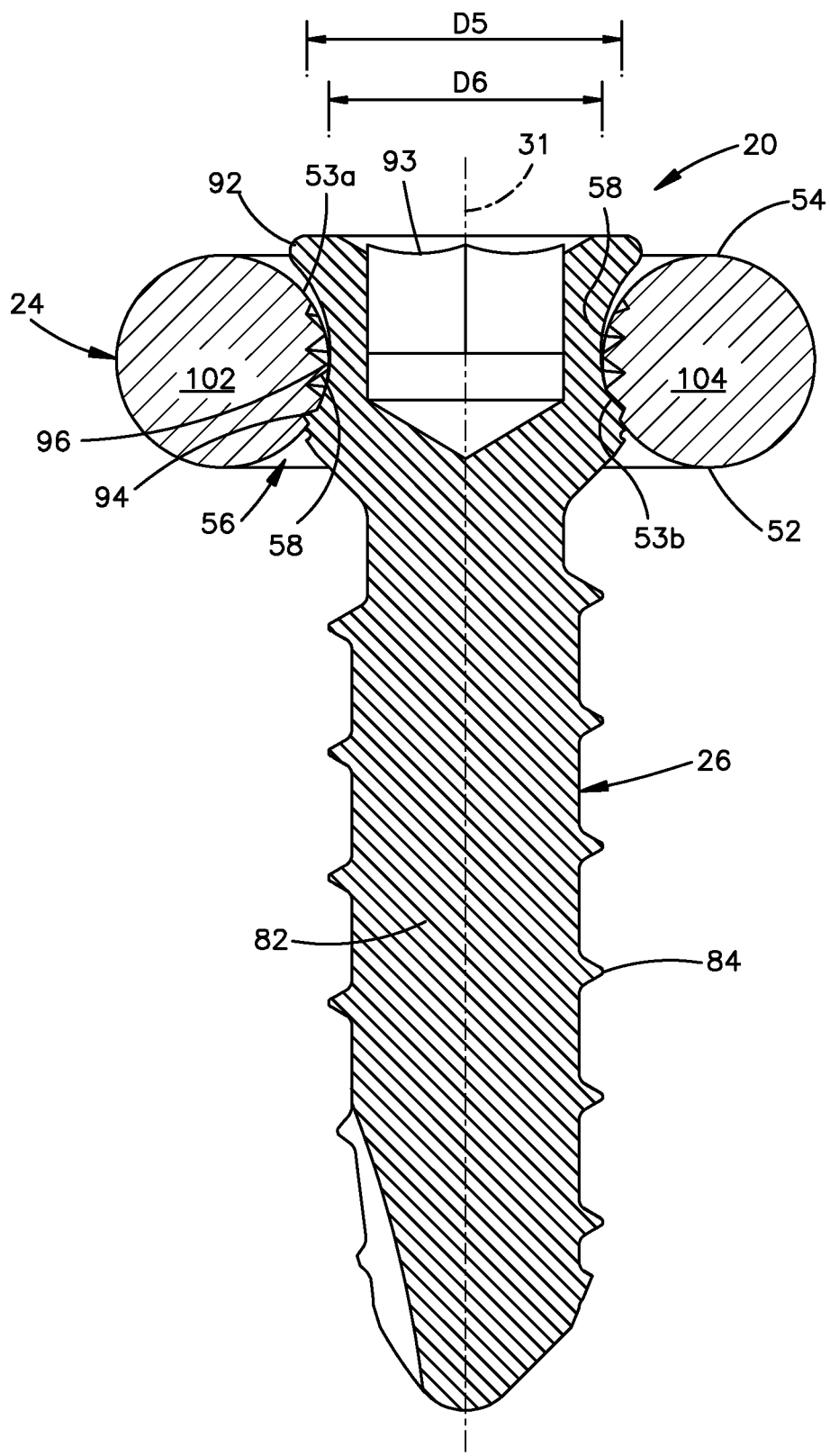
FIG. 6B is a cross-sectional elevation view of the bone fixation system illustrated in FIG. 6A, but showing the bone fixation element secured to the bone implant.

Referring now to FIGS. 6A-6B, it should be appreciated that one or more up to all of the bone fixation elements 26 can be constructed in accordance with an alternative embodiment. For instance, as described above, the bone fixation element 26 includes the head 80 and the shaft 82 that extends in the distal direction with respect to the head 80 along the central axis 31. The shaft 82 can define a length in the transverse direction T that is greater than the length of the head 80 in the transverse direction T. For instance, the shaft 82 can extend directly from the head 80, or the bone fixation element 26 can include a necked region 83 that extends between the head 80 and the shaft 82. Thus, the proximal end 29a of the bone fixation element 26 can be defined by the head 80, and the distal end 29b of the bone fixation element 26 can be defined by the shaft 82. The head 80 can include the ridge 92 which can be defined as a first ridge, and the head 80 can further include a second ridge 94 that is spaced distally from the first ridge 92 in the distal direction along the central axis 31. The head further defines a groove 96 that extends between the first ridge 92 and the second ridge 94. The groove 96 is configured to receive a portion of the inner wall 53 of the bone implant 24 to secure the bone fixation element 26 to the bone implant 24. The groove 96 is recessed into the head 80 toward the central axis 31 between the first and second ridges 92 and 94. Thus, the outer cross-sectional dimension of the head 80 at the groove 96 along a direction that intersects and is perpendicular to the central axis 31 is less than the outer cross-sectional dimension of the head 80 at the first ridge 92, and can further be less than the outer cross-sectional dimension of the head 80 at the second ridge 94. In the illustrated embodiment, the groove 96 is unthreaded, though it should be appreciated that the groove 96 can alternatively be threaded as desired. The cross-sectional dimension of the groove 96 can vary along its length along the transverse direction T. For example, the cross-sectional dimension of the groove 96 can be 3.0 mm, or any suitable alternative dimension between 1.0 mm and 15.0 mm.

The first ridge 92 is configured to engage a portion of the bone implant 24. The first ridge 92 can be generally convex with respect to the central axis 31 so that the first ridge 92 extends outwardly from the central axis 31. Further, the first ridge 92 can be circumferentially disposed about the head 80 and can be round or circular. The ridge 92 can be continuous about the head 80 or segmented as desired. The outer cross-sectional dimension of the first ridge 92, along a direction that is perpendicular to the central axis 31 and intersects the central axis 31, is greater than that of the outer diameter of the bone fixation aperture 56, such that at least a portion of the first ridge 92 is aligned with the bone implant 24 along the transverse direction T parallel to the central axis 31. The outer cross-sectional dimension of the first ridge 92 can range between about 1 mm and about 15 mm, such as about 3.5 mm. When the bone fixation element 26 is fully inserted through the bone fixation aperture 56, the proximal-most surface of the head 80 a proximal-most portion of the upper surface 54 can lie on similar a plane that extends in the longitudinal direction L and the lateral direction A. In alternative embodiments, at least a portion of the first ridge 92 can be linear. Other ridge configurations are possible as desired.

The second ridge 94 is threaded, and thus configured to threadably engage the at least one thread 58 of the bone implant 24 as the bone fixation element 24 is inserted into the bone fixation aperture 56. The second ridge 94 can also be generally convex with respect to the central axis 31 so that the second ridge 94 extends outwardly from the central axis 31. The second ridge 94 can be circumferentially disposed around the head 80, and can be continuous or segmented. The second ridge 94 can define an outer diameter that is substantially equal to the outer diameter of the first ridge 92, though it should be appreciated that the outer diameter of the second ridge 94 can alternatively be less than the outer cross-sectional dimension of the first ridge 92. The outer cross-sectional dimension of the second ridge 94 can range between about 1 and about 15 mm, such as about 3.5 mm.

At least a portion of the second ridge 94 can be threaded so as to threadedly engage with the at least one thread 58 as the bone fixation element 26 is advanced through the bone fixation aperture 56. For instance, the second ridge 94 can define at least one thread 97 that is configured as described above with respect to the at least one thread 88 of the head 80 described above. When the bone fixation element 26 is fully inserted in the bone fixation aperture 56 as illustrated in FIG. 6B, the at least one thread 97 threadably disengages from the at least one thread 58, and is spaced from the at least one thread 58 along the distal direction. When the at least one thread 97 disengages the at least one thread 58, at least a portion of the inner wall 53 of the bone implant 24 is captured or seated between the first ridge 56 and the second ridge 94. Thus, the bone fixation element 26 can be coupled to the bone implant 24 such that at least a portion of the bone implant 24, for instance a portion of the inner wall 53, is captured between 1) a stop surface, which can be defined by the bone fixation element 26, for instance the head 80, and 2) a threaded region of the head 80. For instance, the stop surface can be defined by the ridge 92, and the threaded region can be disposed distal from the ridge 92, and can be defined by the at least one thread 97 of the second ridge 94.

With continuing reference to FIGS. 6A-6B, the groove 96 is configured to receive a portion of the bone implant 24. For instance, at least a portion of the inner wall 53 can be received by the groove 96 between the first and second ridges 92 and 94. As discussed above, the groove 96 can generally conform in shape to the curved inner wall 53 such that the groove 96 is disposed adjacent and can abut the at least one thread 58 when the bone fixation element 26 is inserted in the bone fixation aperture 56. In the illustrated embodiment, the groove 96 is concave and can conform to the convex inner wall 53 as well as portions of the upper surface 54 and bone-facing surface 52. For instance, the concavity of the groove 96 can be defined by a radius of curvature that matches the radius of curvature of the inner wall 53. The second ridge 94 defines a major diameter D6 defined by the crest of the at least one thread 97 that is greater than the minor diameter d1 of the at least one thread 58. Accordingly, when the second ridge 94 is disposed adjacent the at least one thread 58 along the distal direction, the at least one thread 97 of the second ridge 94 is aligned with the at least one thread 58, thereby preventing the head from being removed from the bone implant 24 by translating the bone fixation element 26 along the transverse direction T.

During operation, the shaft 82 of the bone fixation element 26 is driven into the fixation site 28. For instance, the bone fixation element 26 can be rotated in the first direction of rotation so as to advance the shaft 82 into the fixation site 28 in the distal direction, such that the at least one thread 84 threadedly purchases with the fixation site 28. As the bone fixation element 26 advances in the distal direction during rotation in the first direction of rotation, the at least one thread 97 of the second ridge 94 threadedly engages the at least one thread 88 of the head 80. As the bone fixation element 26 rotates in the first direction of rotation after the at least one thread 97 has engaged the at least one thread 54 while the central axis 31 is aligned with the central aperture axis 59, the second ridge 94 threadedly advances distally with respect to the at least one thread 54 until the at least one thread 54, and thus a portion of the inner wall 53, is captured in the groove 96. When the portion of the inner wall 53 is captured in the groove 96, the first and second ridges 92 and 94 movably couple the bone implant 24 to the bone fixation element 26. For instance, the bone fixation element 26 can be further rotated so as to reposition the bone implant 24 along the transverse direction T relative to the fixation site 28. Accordingly, the alignment between the bone implant 24 and the fixation site 28 along the transverse direction T can be adjusted when the bone fixation element 26 is coupled to the bone implant 24.

It should be appreciated that in accordance with one aspect of the present disclosure, a surgical kit can include a plurality of bone implants 24 constructed in accordance with any one or more, up to all, embodiments described herein, and a plurality of bone fixation elements 26 constructed in accordance with any one or more, up to all, embodiments described herein. The kit may also include a drill and a drill guide, and a guidewire. The drill guide (may have a threaded end configured for insertion into the apertures of the bone implant 24, so that a drill can be used to pre-drill a hole into which the bone fixation elements 26 can be inserted.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the processes, machines, manufacture, composition of matter, means, methods, or steps, presently existing or later to be developed that perform substantially the same function or achieve substantially the same result as the corresponding embodiments described herein that may be utilized according to the present disclosure.

What is claimed is:

1. A bone fixation system comprising:
a bone implant including an implant body comprising first and second wire segments that respectively define first and second threaded inner walls that face each other along a lateral direction and collectively define a threaded inner wall,
wherein the implant body defines an outer surface having an upper surface portion, a bone-facing surface portion opposite the upper surface portion, and a convex surface portion extending between the threaded inner wall and the upper surface portion,
the implant body further defining a bone fixation aperture that extends through the implant body from the upper surface portion to the bone-facing surface portion along a distal direction that is substantially perpendicular to the lateral direction, the bone fixation aperture at least partially defined by the threaded inner wall, wherein the convex surface portion is convex in a plane defined by the lateral and distal directions; and
a bone fixation element including a head and a shaft that extends with respect to the head in the distal direction and is configured to be driven into a fixation site,
wherein the bone fixation element further defines a stop surface and the head defines at least one thread that is spaced from the stop surface in the distal direction, the at least one thread is configured to threadedly engage the threaded inner wall as the bone fixation element rotates to threadedly advance the head in the distal direction in the bone fixation aperture, and the at least one thread of the head defines a major diameter that is less than a major diameter of the threaded inner wall such that a gap is defined between the at least one thread of the head and the threaded inner wall along a line extending along the distal direction, wherein, when the at least one thread is threadedly engaged with the threaded inner wall of the bone implant, at least a portion of each of the threaded inner wall and the convex surface portion is captured between the stop surface and the at least one thread of the head, and the stop surface is configures to compress the at least a portion of each of the threaded inner wall and the convex surface portion as the head threadedly advances in the bone fixation aperture, wherein the at least one thread of the head comprises a first surface and a second surface, such that, when the head distally advances in the bone fixation aperture, the second surface becomes a leading surface and the first surface becomes a trailing surface, and wherein, during the compression, the head is moveable in the bone fixation aperture (1) from a first position in which a first portion of the gap is defined between the trailing surface and the threaded inner wall and a second portion of the gap is defined between the leading surface and the threaded inner wall, (2) to a second position in which an entirety of the gap is disposed between the leading surface and the threaded inner wall.

2. The bone fixation system as recited in claim 1, wherein the stop surface is aligned with the bone implant in the distal direction when the at least a portion of each of the threaded inner wall and the convex surface portion is captured between the stop surface and the at least one thread.

3. The bone fixation system as recited in claim 2, wherein rotation of the bone fixation element after the at least one thread has threadedly engaged the threaded inner wall brings the stop surface into contact with the bone implant.

4. The bone fixation system as recited in claim 3, wherein further rotation of the bone fixation element when the stop surface is in contact with the bone implant drives the stop surface in the distal direction, thereby compressing the threaded inner wall and the at least a portion of the convex surface portion against the at least one thread.

5. The bone fixation system as recited in claim 4, wherein further rotation of the bone fixation element compresses the threaded inner wall against the leading surface.

6. The bone fixation system as recited in claim 5, wherein the stop surface is defined by a ridge that defines an outer cross-sectional dimension, and the major diameter of the head is less than the outer cross-sectional dimension.

7. The bone fixation system as recited in claim 6, wherein the head defines the ridge.

8. The bone fixation system as recited in claim 6, wherein after the ridge is in contact with the bone implant, the head defines a proximal-most surface and a distal-most surface, and the proximal-most surface does not project out with respect to the bone implant in a proximal direction that is opposite the distal direction.

9. The bone fixation system as recited in claim 4, wherein, from the second positionof the head in the bone fixation aperture: 1) contact between the bone implant and the at least one thread prevents the bone implant from moving relative to the bone fixation element in the distal direction, and 2) contact between the convex surface portion of the bone implant and the stop surface prevents the bone implant from moving relative to the bone fixation element in a proximal direction that is opposite the distal direction.

10. The bone fixation system as recited in claim 1, wherein the bone implant comprises a bone plate.

11. The bone fixation system as recited in claim 1, wherein the shaft comprises at least one thread that is configured for threaded purchase in the fixation site as the head threadedly advances in the bone fixation aperture.

12. The bone fixation system as recited in claim 1, wherein the bone fixation element is elongate within a central axis, the stop surface is defined by a ridge that defines an outer cross-sectional dimension in a direction that intersects the central axis and is perpendicular to the central axis, and the major diameter of the at least one thread is less than the outer cross-sectional dimension of the ridge.

13. The bone fixation system as recited in claim 12, wherein the shaft defines at least one thread configured to threadedly purchase with underlying bone as the shaft is rotatably driven into the underlying bone.

14. The bone fixation system as recited in claim 13, wherein the at least one thread of the head defines a lead, and the at least one thread of the shaft defines a lead that is equal to the lead of the at least one thread of the head.

15. The bone fixation system as recited in claim 13, wherein the at least one thread of the head defines a lead, and the at least one thread of the shaft defines a lead that is greater than the lead of the at least one thread of the head.

16. A bone fixation system comprising:

an implant body that includes first and second wire segments that are spaced from each other along a lateral direction in a manner collectively defining a bone fixation aperture along a distal direction and a threaded inner wall within the bone fixation aperture, wherein the distal direction is offset from the lateral direction, and the first and second wire segments each define an upper surface and a convex outer surface extending from the threaded inner wall and the upper surface; and a bone fixation element including a head and a shaft that extends with respect to the head in the distal direction, wherein the head defines a stop surface and at least on thread that is spaced from the stop surface in the distal direction, wherein the at least one thread is configured to threadedly engage the threaded inner wall such that, as the head threadedly advances in the distal direction in the bone fixation aperture, the stop surface contacts the convex outer surface and subsequently compresses at least a portion of each of the threaded inner wall and the convex outer surface against at least one thread, and wherein the first and second wire segments define a first neck at a first end of the bone fixation aperture and a second neck at a second end of the bone fixation aperture opposite the first end along a longitudinal direction, the longitudinal direction is substantially perpendicular to the lateral direction and offset from the distal direction, and the first and second wire segments each continuously extend from the first neck to the second neck along a shared plane that includes the lateral and longitudinal directions.

17. The bone fixation system as recited in claim 16, wherein the at least one thread defines a leading surface and a trailing surface, the leading surface is spaced from the trailing surface in the distal direction, and the at least one thread is further configured to threadedly engage the threaded inner wall such that, as the head threadedly advances in the distal direction in the bone fixation aperture, a gap is defined between the at least a portion of the threaded inner wall and the leading surface of the at least one thread while the at least a portion of the threaded inner wall contacts the trailing surface of the at least one thread.

18. The bone fixation system as recited in claim 17, wherein 1) contact between the at least a portion of the threaded inner wall and the trailing surface of the at least one thread prevents the bone implant from moving relative to the bone fixation element in the distal direction, and 2) contact between the convex surface portion and the stop surface prevents the bone implant from moving relative to the bone fixation element in a proximal direction that is opposite the distal direction.

19. A bone fixation system, comprising:
  an implant body that includes first and second wire segments that are spaced from each other along a lateral direction in a manner collectively defining a bone fixation aperture along a distal direction and a threaded inner wall within the bone fixation aperture, wherein the distal direction is offset from the lateral direction, and the first and second wire segments each define an upper surface and a convex outer surface extending from the threaded inner wall and the upper surface; and
  a bone fixation element including a head and a shaft that extends with respect to the head in the distal direction, wherein the head defines a stop surface and at least one thread that is spaced from the stop surface in the distal direction,
  wherein the at least one thread has a trailing surface and a leading surface disposed in the distal direction with respect to the trailing surface, and the at least one thread of the head and the threaded inner wall of the implant body are cooperatively configured such that rotation of the bone fixation element within the bone fixation aperture threadedly advances the bone fixation element and drives the stop surface in the distal direction, thereby 1) compressing at least a portion of the threaded inner wall and at least a portion of the convex outer surface against the at least one thread, such that the at least a portion of the threaded inner wall contacts the trailing surface of the at least one thread, and 2) during the compression, advancing the head from a first position, in which a first portion of a gap is defined between the trailing surface and the threaded inner wall and a second portion of the gap is defined between the leading surface and the threaded inner wall, to a second position in which the gap is disposed between the leading surface and the threaded inner wall.

* * * * *